(12) United States Patent
Nakamura et al.

(10) Patent No.: US 7,906,616 B2
(45) Date of Patent: Mar. 15, 2011

(54) TRUNCATED DANCE, DANCE COMPLEX AND METHOD OF USING THESE

(75) Inventors: Tomoyuki Nakamura, Kyoto (JP); Maretoshi Hirai, Kyoto (JP)

(73) Assignee: Kansai Medical University, Osaka (JP)

( * ) Notice: Subject to any disclaimer, the term of this patent is extended or adjusted under 35 U.S.C. 154(b) by 47 days.

(21) Appl. No.: 10/594,339

(22) PCT Filed: Mar. 4, 2005

(86) PCT No.: PCT/JP2005/004274
§ 371 (c)(1),
(2), (4) Date: Oct. 17, 2006

(87) PCT Pub. No.: WO2005/093057
PCT Pub. Date: Oct. 6, 2005

(65) Prior Publication Data
US 2007/0218003 A1 Sep. 20, 2007

(30) Foreign Application Priority Data
Mar. 29, 2004 (JP) .................................. 2004-096685

(51) Int. Cl.
*C07K 14/00* (2006.01)
(52) U.S. Cl. ...................................................... 530/300
(58) Field of Classification Search ........................ None
See application file for complete search history.

(56) References Cited

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Nakamura et al, Fibulin-5/DANCE is essential for elastogenesis in vivo. Nature. Jan. 10, 2002;415(6868):171-5.*
Kowal et al, EVEC, a novel epidermal growth factor-like repeat-containing protein upregulated in embryonic and diseased adult vasculature. Circ Res. May 28, 1999;84(10):1166-76.*
USPTO in house BLAST alignment SEQ ID No. 2 with AF137350 performed Aug. 18, 2008.*
van der Flier et al, Function and interactions of integrins. Cell Tissue Res. Sep. 2001;305(3):285-98.*
T. Nakamura et al., "DANCE, A Novel Secreted RGD Protein Expressed in Developing, Atherosclerotic, and Balloon-Injured Arteries", J. Biol. Chem., vol. 274, No. 32, pp. 22476-22483, Aug. 6, 1999.
X. Liu et al., "Elastic Fiber Homeostasis Requires Lysyl Oxidase-Like 1 Protein", Nature Genetics, vol. 36, No. 2, pp. 178-182, Feb. 2004.

B. Loeys et al., "Homozygosity for a Missense Mutation in Fibulin-5 (FBLN5) Results in a Severe Form of Cutis Laxa", Human Molecular Genetics, vol. 11, No. 18, pp. 2113-2118, 2002.
D. Markova et al., "Genetic Heterogeneity of Cutis Laxa: A Heterozygous Tandem Duplication within the Fibulin-5 (FBLN5) Gene", Am. J. Hum. Genet., vol. 72, pp. 998-1004, 2003.
European Partial Search Report dated Aug. 9, 2007 in conjunction with EP application No. 05720545.2-2401 which is a counterpart to the present application.
Sasaki, T. et al., "Different susceptibilities of fibulin-1 and fibulin-2 to cleavage by matrix metalloproteinases and other tissue proteases", Euro. J. Biochem., vol. 240, No. 2, pp. 427-434, 1996.
Hirai, M. et al., "Fibulin-5/DANCE has an elastogenic organizer activity that is abrogated by proteolytic cleavage in vivo, The Journal of Cell Biology", vol. 176, No. 7, pp. 1061-1071, 2007.
Nakamura, T., Molecular Cardiovascular Medicine, vol. 3., No. 5, pp. 547-554, 2002.
Kuang P. et al., "Coordinate expression of fibulin-5/DANCE and elastin during lung injury repair", Am. J. Physiol. Lung Cell Mol. Physiol., vol. 285, No. 5, pp. L1147-1152, 2003.
Tsuruga, E. et al., "Induction of fibulin-5 gene is regulated by tropoelastin gene, and correlated with tropoelastin accumulation in vitro", The International Journal of Biochemistry & Cell Biology, vol. 36, No. 3, pp. 395-400, 2004.
Schiemann, W. P. et al., "Context-specific Effects of Fibulin-5 (DANCE/EVEC) on Cell Proliferation, Motility, and Invasion", The Journal of Biological Chemistry, vol. 277, No. 30, pp. 27367-27377, 2002.
Midwood, K. S. And Schwarzbauer, J. E., "Elastic Fibers: Building Bridges Between Cells and Their Matrix", Current Biology, vol. 12, No. 8, pp. R279-R281, 2002.
Yanagisawa, H. et al., "Fibulin-5 is an elastin-binding protein essential for elastic fibre development in vivo", Nature, vol. 415, pp. 168-171, 2002.
Nakamura, T. et al., "Fibulin-5/DANCE is essential for elastogenesis in vivo", Nature, vol. 415, pp. 171-175, 2002.
G. Kostka, Apr. 2005, European Molecular Biology Laboratory, Accession No. AJ133490.

* cited by examiner

*Primary Examiner* — Sheridan Swope
(74) *Attorney, Agent, or Firm* — Wenderoth, Lind & Ponack, L.L.P.

(57) ABSTRACT

A method of screening for a medicine capable of regulating generation of elastic fibrous tissue; and various means that are requisite for the method. In particular, the invention includes a polypeptide obtained by cleaving DANCE and a polynucleotide coding for the polypeptide; a method of cleaving DANCE; an antibody against the polypeptide obtained by cleaving DANCE; a method of measuring the amount of DANCE cleavage and a kit therefore; a DANCE variant and its polynucleotide; various DANCE complexes and a method of preparing such; a method of screening for a substance capable of regulating DANCE or a DANCE-specific protease, and a substance obtained by such screening method; an agent for regulating generation of elastic fibrous tissue; and a kit with DANCE and a polynucleotide coding for the same.

1 Claim, 8 Drawing Sheets

TRUNCATED DANCE, DANCE COMPLEX AND METHOD OF USING THESE

This application is a U.S. national stage of International Application No. PCT/JP2005/004274 filed Mar. 4, 2005.

TECHNICAL FIELD

The present invention relates to a polypeptide obtained by cleaving DANCE and a polynucleotide that encodes the same; a method of cleaving DANCE; an antibody against a polypeptide obtained by cleaving DANCE; a method and kit for measuring the amount of DANCE cleaved; a DANCE mutant and a polynucleotide that encodes the same; various DANCE complexes and a method of preparing the same; a screening method for a substance capable of regulating the activity of DANCE or a DANCE-specific protease, and the substance obtained thereby; an agent for regulating the formation of elastic fibers; and a kit comprising at least DANCE or a polynucleotide that encodes the same, and the like.

BACKGROUND ART

Elastic fibers are extracellular fibers responsible for the elasticity of highly flexible tissues such as the lungs, arteries, and skins. The major feature of human aging is a loss of tissue elasticity, which results in pulmonary edema, arterial sclerosis and snaking, skin loosening, and the like. These are increasingly important challenges in the aging society, many of which are caused by deterioration or rupture of elastic fibers. Despite the importance of elastic fibers, details of the molecular mechanisms of elastic fiber formation and deterioration remain unclear.

During the formation of elastic fibers, it is important that elastin deposits along fibers called microfibril and is crosslinked by enzymes of the lysyl oxidase family [lysyl oxidase (LOX), lysyl oxidase-like (LOXL) 1-4] [Molnar, J. et al., Biochim Biophys Acta 1647: 220-4 (2003); Rosenbloom, J. et al., Faseb J. 7: 1208-18. (1993)]. However, only a little is known about the molecular mechanisms based on which this process occurs in a living organism. Although microfibril is reported to essentially comprise long high-molecular proteins such as fibrillin 1, fibrillin 2, and LTBP2 (latent TGFb-binding protein 2), fibrillin 1 or fibrillin 2 gene knockout mice are free from elastic fiber abnormalities; therefore, contribution of these proteins to the formation of elastic fibers is unlikely [Pereira, L. et al., Nat. Genet. 17: 218-22 (1997), Putnam, E. A. et al., Nat. Genet. 11: 456-8 (1995), Chaudhry, S. S. et al., Mol. Genet. 10: 835-43 (2001)], and it remains unknown whether or not LTBP2 contributes to the formation of elastic fibers because LTBP2 gene knockout mice are fatal in early fetal period [Shipley, J. M. et al., Mol. Cell Biol. 20: 4879-87 (2000)].

The present inventors cloned a secretory protein known as DANCE (developmental arteries and neural crest epidermal growth factor (EGF)-like; also referred to as fibulin-5) using the signal sequence trap method [Nakamura, T. et al., J. Biol. Chem. 274: 22476-83 (1999)], prepared knockout mice lacking the expression of the protein, and found that elastic fibers in the whole body have been disjoined [Nakamura, T. et al., Nature 415: 171-5 (2002)]. For this reason, the phenotype of DANCE gene-deficient mice is highly similar to human aging, showing a lack of elasticity and loosening of the skin, severe pulmonary edema, and arterial tortuosity and sclerosis. Hence, DANCE is an essential protein for the formation of elastic fibers. Also, the present inventors have shown that the binding of DANCE to integrin can play an important role in living organisms [Nakamura, T. et al., J. Biol. Chem. 274: 22476-83 (1999)].

Recently, it was reported that knockout mice lacking the expression of LOXL1, one of the elastin-crosslinking enzymes, like DANCE knockout mice, exhibited abnormalities of the formation of elastic fibers [Liu, X. et al., Nat. Genet. 36: 178-82 (2004)]. Because LOXL1 binds to DANCE, and also because LOXL1 is no longer localized on elastic fibers in DANCE knockout mice, it is postulated that DANCE serves as an adapter to anchor the LOXL1 enzyme at a due position. Because the phenotype of LOXL1 knockout mice is weaker and emerges slightly later than the phenotype of DANCE knockout mice, the role of DANCE is considered to be more than anchoring LOXL1; the finding that DANCE defines the localization of the elastin-crosslinking enzyme is important in understanding the molecular mechanism by which DANCE contributes to the formation of elastic fibers.

However, in view of the fact that elastic fibers are formed along microfibril, it is considered that the binding of DANCE to the elastin-crosslinking enzyme is insufficient, and that DANCE needs to bind to a microfibril constituent protein. However, it remains unknown to which one of the microfibril proteins DANCE binds. Elucidating the detailed functions of DANCE is strongly demanded since it would enable the development of a pharmaceutical having a new mechanism of action enabling the regulation of the formation of elastic fibers.

DISCLOSURE OF THE INVENTION

Accordingly, it is an object of the present invention to provide a screening method that enables the development of a pharmaceutical capable of regulating the formation of elastic fibers on the basis of a newly elucidated function of DANCE, a diagnostic method for conditions of the formation of elastic fibers, and various means necessary for the screening method and diagnostic method, and the like.

The present inventors conducted diligent investigations aiming at solving the above-described problems, and found that DANCE undergoes partial cleavage to cause a functional change in a living organism. A cleaved form of DANCE has lost the capability of binding to cell surface integrin and the capability of binding to each other, and has acquired the greater capability of binding to LTBP2, which is a microfibril constituent protein. Therefore, cleavage of DANCE is considered to be important to the regulation of the formation of elastic fibers.

The present inventors also found that DANCE binds to LTBP2, that DANCE binds to each other, and that DANCE binds to lysyl oxidase. The binding of DANCE to these proteins is considered to be important to the regulation of the formation of elastic fibers.

The present inventors developed the present invention based on the above findings. Accordingly, the present invention provides the following:

<1> a polypeptide obtained by cleaving DANCE with a DANCE-specific protease, which consists of substantially the same amino acid sequence as the amino acid sequence shown by SEQ ID NO:6.
<2> a polypeptide consisting of the amino acid sequence shown by SEQ ID NO:6.
<3> a polynucleotide having a nucleotide sequence that encodes the polypeptide <1> above.
<4> a polynucleotide consisting of the nucleotide sequence shown by SEQ ID NO:5.

<5> a polypeptide obtained by cleaving DANCE with a DANCE-specific protease, which consists of substantially the same amino acid sequence as the amino acid sequence shown by SEQ ID NO:8.
<6> a polypeptide consisting of the amino acid sequence shown by SEQ ID NO:8.
<7> a polynucleotide having a nucleotide sequence that encodes the polypeptide <5> above.
<8> a polynucleotide consisting of the nucleotide sequence shown by SEQ ID NO:7.
<9> a method of cleaving DANCE, which comprises contacting DANCE with a DANCE-specific protease.
<10> an antibody having specific affinity for the polypeptide <1> or <2> above.
<11> a monoclonal antibody having specific affinity for the polypeptide <5> or <6> above.
<12> a method comprising measuring the amount of DANCE cleaved in a biological sample from an animal.
<13> a kit for measuring the amount of DANCE cleaved, which comprises an anti-DANCE antibody.
<14> a DANCE mutant incorporating an amino acid mutation in the DANCE cleavage site with a DANCE-specific protease so that the mutant exhibits resistance to the protease.
<15> a polynucleotide having a nucleotide sequence that encodes the polypeptide <14> above.
<16> a DANCE complex comprising at least two DANCEs.
<17> the complex <16> above which comprises at least two kinds of DANCE which are distinguishable forms.
<18> the complex <16> or <17> above, which further comprises lysyl oxidase and/or LTBP2.
<19> a DANCE complex comprising at least one DANCE and lysyl oxidase and/or LTBP2.
<20> a method of preparing a DANCE complex comprising at least two DANCEs, which comprises contacting at least two DANCEs to form a complex.
<21> a method of preparing a DANCE complex comprising at least one DANCE and lysyl oxidase and/or LTBP2, which comprises contacting at least one DANCE with lysyl oxidase and/or LTBP2 to form a complex.
<22> a screening method for a substance capable of regulating the activity of a DANCE-specific protease, which comprises the following steps (a), (b) and (c):
(a) contacting a test substance with the DANCE-specific protease;
(b) measuring the activity of the DANCE-specific protease resulting from the step (a) above, and comparing the activity with an activity of a DANCE-specific protease obtained without contacting the test substance;
(c) selecting a test substance that regulates the activity of the DANCE-specific protease on the basis of the results of the comparison in (b) above.
<23> the method <22> above which is a method for identifying a regulator of the formation of elastic fibers.
<24> a screening method for a substance capable of regulating the activity of a DANCE-specific protease, which comprises the following steps (a), (b) and (c):
(a) administering a test substance to an animal;
(b) measuring the activity of the DANCE-specific protease resulting from the step (a) above, and comparing the activity with an activity of the DANCE-specific protease obtained without administering the test substance;
(c) selecting a test substance that regulates the activity of the DANCE-specific protease on the basis of the results of the comparison in (b) above.

<25> a screening method for a substance capable of regulating the formation of a DANCE complex comprising at least two DANCEs, which comprises the following steps (a), (b) and (c):
(a) contacting at least two DANCEs in the presence of a test substance;
(b) measuring the amount of the DANCE complex resulting from the step (a) above, and comparing the amount with the amount of the DANCE complex obtained in the absence of the test substance;
(c) selecting a test substance that regulates the formation of the DANCE complex on the basis of the results of the comparison in (b) above.
<26> the method <25> above wherein at least two kinds of DANCE which are distinguishable forms are used.
<27> a screening method for a substance capable of regulating the formation of a DANCE complex comprising at least one DANCE and lysyl oxidase and/or LTBP2, which comprises the following steps (a), (b) and (c):
(a) contacting at least one DANCE with lysyl oxidase and/or LTBP2 in the presence of a test substance;
(b) measuring the amount of the DANCE complex resulting from the step (a) above, and comparing the amount with the amount of the DANCE complex obtained in the absence of the test substance;
(c) selecting a test substance that regulates the formation of the DANCE complex on the basis of the results of the comparison in (b) above.
<28> a regulator of the formation of elastic fibers obtained by the method of any of the <23> to <27> above.
<29> a screening method for a DANCE-specific protease with DANCE cleavage activity as the index.
<30> a DANCE-specific protease obtained by the method <29> above.
<31> a polynucleotide having a nucleotide sequence that encodes the DANCE-specific protease obtained by the method <29> above.
<32> an agent for regulating the formation of elastic fibers comprising the DANCE-specific protease <30> above or the polynucleotide <31> above.
<33> a kit comprising the following (a) and (b):
(a) DANCE or a polynucleotide having a nucleotide sequence that encodes DANCE;
(b) at least one of the following components (i) to (vi);
(i) DANCE which is a distinguishable form from the DANCE (a);
(ii) a polynucleotide having a nucleotide sequence that encodes DANCE which is a distinguishable form from the DANCE (a);
(iii) lysyl oxidase;
(iv) a polynucleotide having a nucleotide sequence that encodes lysyl oxidase;
(v) LTBP2;
(vi) a polynucleotide having a nucleotide sequence that encodes LTBP2.
<34> a method of identifying a cell expressing a DANCE-specific protease, which comprises the following steps (a) to (b):
(a) contacting DANCE with a certain animal cell;
(b) determining whether or not the DANCE is cleaved.

A screening method of the present invention is useful for enabling the development of a pharmaceutical of a new mechanism of action allowing the regulation of the formation of elastic fibers, or the identification of a DANCE-specific protease. The assay method of the present invention is useful for enabling the diagnosis of the status of the formation of elastic fibers. Furthermore, the polypeptide, complex and kit of the present invention are preferably used for performing the method of the present invention, for preventing, treating or improving a condition for which regulation of the formation of elastic fibers is desired, or as a research/diagnostic reagent and the like.

DETAILED DESCRIPTION OF THE INVENTION

Figure 1:
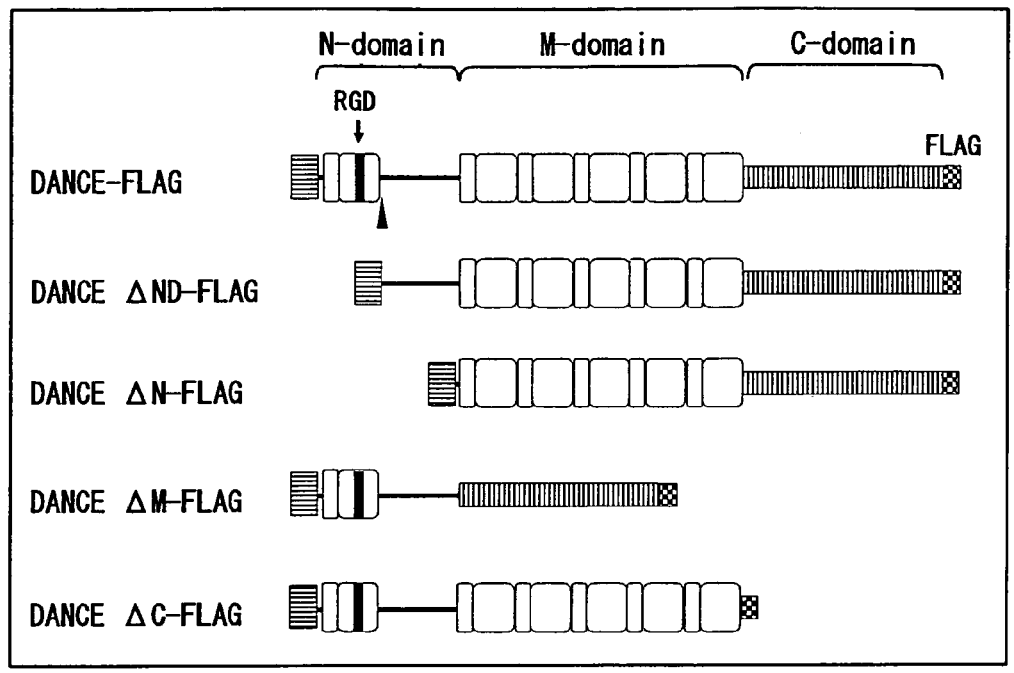
FIG. 1 shows the constructs of DANCE-deleted mutants. Lateral line box: signal sequence; open box: calcium-binding EGF-like (cbEGF) motif; filled box: RGD motif; vertical line box: C-terminal domain; oblique line box: FLAG tag.

1. Cleaved Forms of DANCE and Polynucleotides that Encode the Same

The present invention provides polypeptides obtained by cleaving DANCE with a DANCE-specific protease, and polynucleotides that encode the polypeptides.

"DANCE" refers to a polypeptide consisting of the amino acid sequence shown by SEQ ID NO:2 or the amino acid sequence shown by SEQ ID NO:4 (an amino acid sequence resulting from the removal of the putative signal sequence from the amino acid sequence shown by SEQ ID NO:2), or an equivalent thereto (for example, a variant comprising SNP or haplotype, a mammalian orthologue and the like). Specifically, an equivalent to a polypeptide consisting of the amino acid sequence shown by SEQ ID NO:2 or SEQ ID NO:4 is a polypeptide having substantially the same amino acid sequence as the amino acid sequence shown by SEQ ID NO:2 or SEQ ID NO:4, and cleaved with a DANCE-specific protease. The present inventors found that in the present invention, DANCE as such is cleaved with a DANCE-specific protease, and, based on this finding, succeeded in providing new polypeptides obtained by cleaving DANCE.

The mammalian orthologue of DANCE is not particularly limitated; for example, bovine, sheep, swine, goat, monkey, rabbit, rat, hamster, guinea pig, and mouse orthologues are preferable, with greater preference given to a human, monkey, rat or mouse orthologue.

As used herein, "DANCE-specific protease" refers to a protease that cleaves a DANCE consisting of the amino acid sequence shown by SEQ ID NO:2 between the 77th amino acid and the 78th amino acid therein. A DANCE-specific protease is characterized by inhibition by aprotinine, which is a serine protease inhibitor, and non-inhibition by E64, which is a cysteine protease inhibitor. Also, it has been confirmed that a DANCE-specific protease is expressed in skin fibroblasts, 293T cells, lung tissue and the like. Furthermore, it has been confirmed that a DANCE-specific protease has a decreased capability of cleaving the mutated form of DANCE wherein the 77th arginine residue has been substituted with the alanine residue.

Therefore, one of the polypeptides of the present invention obtained by cleavage of DANCE with a DANCE-specific protease is a polypeptide consisting of an amino acid sequence corresponding to the 24th to 77th amino acids in the amino acid sequence shown by SEQ ID NO:2 (i.e., the amino acid sequence shown by SEQ ID NO:6), or an equivalent thereto. Specifically, an equivalent to a polypeptide consisting of the amino acid sequence shown by SEQ ID NO:6 is a polypeptide having substantially the same amino acid sequence as the amino acid sequence shown by SEQ ID NO:6.

Another polypeptide resulting from the cleavage of DANCE, provided by the present invention, is a polypeptide consisting of an amino acid sequence corresponding to the 78th to 448th amino acids in the amino acid sequence shown by SEQ ID NO:2 (i.e., the amino acid sequence shown by SEQ ID NO:8), or an equivalent thereto. Specifically, an equivalent to a polypeptide consisting of the amino acid sequence shown by SEQ ID NO:8 is a polypeptide having substantially the same amino acid sequence as the amino acid sequence shown by SEQ ID NO:8.

Substantially the same amino acid sequence as the amino acid sequence shown by SEQ ID NO:6 or SEQ ID NO:8 is an amino acid sequence resulting from the substitution, deletion, insertion, or addition of one or two or more (for example, 1 to 30, preferably 1 to 20, more preferably 1 to 10, most preferably 1 to 5) amino acids in the amino acid sequence shown by SEQ ID NO:6 or SEQ ID NO:8.

As substantially the same amino acid sequence as the amino acid sequence shown by SEQ ID NO:6 or SEQ ID NO:8, an amino acid sequence having an identity of about 70% or more, preferably about 80% or more, more preferably about 90% or more, still more preferably about 95% or more, even still more preferably about 97% or more, and most preferably 99% or more, to the amino acid sequence shown by SEQ ID NO:6 or 8, can be used. Identity (%) can be determined using a program in common use in the art (for example, BLAST, FASTA and the like) in default settings. In another aspect, identity (%) can be determined using any algorithm known in the art, for example, the algorithm of Needleman et al. (1970) (J. Mol. Biol. 48: 444-453), the algorithm of Myers and Miller (CABIOS, 1988, 4: 11-17) and the like. The algorithm of Needleman et al. is incorporated in the GAP program in the GCG software package (available from www.gcg.com), and identity (%) can be determined using, for example, BLOSUM 62 matrix or PAM250 matrix, and gap weight: 16, 14, 12, 10, 8, 6 or 4, and length weight: 1, 2, 3, 4, 5 or 6. The algorithm of Myers and Miller is incorporated in the ALIGN program, which is part of the GCG sequence alignment software package. When utilizing the ALIGN program to compare amino acid sequences, for example, PAM120 weight residue table, gap length penalty 12 and gap penalty 4 can be used.

Each of the polypeptides consisting of substantially the same amino acid sequence as the amino acid sequence shown by SEQ ID NO:6 or SEQ ID NO:8 preferably retains the same quality of activity as the corresponding polypeptide consisting of substantially the same amino acid sequence as the amino acid sequence shown by SEQ ID NO:6 or SEQ ID NO:8 (as used herein, "activity" has the same definition as function). "The same quality of activity" means that the activities are qualitatively equivalent to each other; although the activities are preferably quantitatively equivalent to each other as well, they may differ in an acceptable range (for example, about 0.5 to about 2 times).

As examples of the same quality of activity as a polypeptide consisting of the amino acid sequence shown by SEQ ID NO:6, integrin-binding activity and homo-complex formation activity (in other words, binding activity between DANCEs) can be mentioned. Therefore, the polypeptide consisting of substantially the same amino acid sequence as the amino acid sequence shown by SEQ ID NO:6 preferably retains the consensus Arg-Gly-Asp (RGD) motif (an amino acid sequence corresponding to the 31st to 33rd amino acids in the amino acid sequence shown by SEQ ID NO:6), which is the integrin-binding site, and/or a homo-complex formation site. The accurate position of the homo-complex formation site can be identified by a method known per se, such as deletion analysis.

As a preferable example of the polypeptide consisting of substantially the same amino acid sequence as the amino acid sequence shown by SEQ ID NO:6, a polypeptide consisting of the amino acid sequence shown by SEQ ID NO:10 (mouse orthologue) and a polypeptide consisting of the amino acid sequence shown by SEQ ID NO:14 (rat orthologue) can be mentioned.

As examples of the same quality of activity as a polypeptide consisting of the amino acid sequence shown by SEQ ID NO:8, lysyl oxidase-binding activity, lysyl oxidase-like-1-binding activity, LTBP2-binding activity and the like can be mentioned. Therefore, the polypeptide consisting of substantially the same amino acid sequence as the amino acid sequence shown by SEQ ID NO:8 preferably retains at least one or more, preferably two or more, and more preferably all, of the lysyl oxidase-binding site, the lysyl oxidase-like-1-binding site, and the LTBP2 (latent TGF-β-binding protein 2)-binding site. For example, the LTBP2-binding site is considered to be present in a domain wherein the calcium-binding EGF (cbEGF)-like motif exists in a series at the center of DANCE [representatively, (D/N)X(D/N) (E/Q)$X_m$(D/N)*$X_n$ (Y/F): wherein m and n are variables, and the asterisk represents β hydroxylation] (see, for example, Example 6), and the more accurate positions of the lysyl oxidase-binding site, the lysyl oxidase-like-1-binding site, and the LTBP2-binding site can be determined by a method known per se such as deletion analysis.

As a preferable example of the polypeptide consisting of substantially the same amino acid sequence as the amino acid sequence shown by SEQ ID NO:8, a polypeptide consisting of the amino acid sequence shown by SEQ ID NO:12 (mouse orthologue) and a polypeptide consisting of the amino acid sequence shown by SEQ ID NO:16 (rat orthologue) can be mentioned.

The present invention also provides a polynucleotide that encodes a polypeptide consisting of the amino acid sequence shown by SEQ ID NO:6 or SEQ ID NO:8 or an equivalent thereto. The polynucleotide of the present invention may be DNA or RNA.

As a preferable example of the polynucleotide that encodes a polypeptide consisting of the amino acid sequence shown by SEQ ID NO:6 or SEQ ID NO:8, a polynucleotide consisting of the nucleotide sequence shown by SEQ ID NO:5 or SEQ ID NO:7 can be mentioned.

In another aspect, the polynucleotide that encodes an equivalent to a polypeptide consisting of the amino acid sequence shown by SEQ ID NO:6 is a polynucleotide that hybridizes to a complementary sequence of the nucleotide sequence shown by SEQ ID NO:5 under high stringent conditions, but does not hybridize to a complementary sequence of the nucleotide sequence shown by SEQ ID NO:7 under high stringent conditions (preferably moderate stringent conditions).

The polynucleotide that encodes an equivalent to a polypeptide consisting of the amino acid sequence shown by SEQ ID NO:8 can be a polynucleotide that hybridizes to a complementary sequence of the nucleotide sequence shown by SEQ ID NO:7 under high stringent conditions, but does not hybridize to a complementary sequence of the nucleotide sequence shown by SEQ ID NO:5 under high stringent conditions (preferably moderate stringent conditions).

Conditions for the above-described hybridization can be established with reference to conditions as previously reported (Current Protocols in Molecular Biology, John Wiley & Sons, 6.3.1-6.3.6, 1999). For example, as conditions for hybridization under high stringent conditions, 6×SSC (sodium chloride/sodium citrate)/45° C. followed by not less than one time of washing with 0.2×SSC/0.1% SDS/50-65° C. can be mentioned. As examples of conditions for hybridization under moderate stringent conditions, 2×SSC/30° C. followed by not less than one time of washing with 1×SSC/0.1% SDS/30-50° C. can be mentioned.

As a preferable example of the polynucleotide that encodes an equivalent to a polypeptide consisting of the amino acid sequence shown by SEQ ID NO:6, a polynucleotide consisting of the nucleotide sequence shown by SEQ ID NO:9 (mouse orthologue) and a polynucleotide consisting of the nucleotide sequence shown by SEQ ID NO:13 (rat orthologue) can be mentioned.

As a preferable example of the polynucleotide that encodes an equivalent to a polypeptide consisting of the amino acid sequence shown by SEQ ID NO:8, a polynucleotide consisting of the nucleotide sequence shown by SEQ ID NO:11 (mouse orthologue) and a polynucleotide consisting of the nucleotide sequence shown by SEQ ID NO:15 (rat orthologue) can be mentioned.

2. Methods of Preparing Cleaved Forms of DANCE and Polynucleotides that Encode the Same

2.1. Non-Cleaving Method

A polynucleotide of the present invention can be prepared by a method known per se. For example, the polynucleotide that encodes a polypeptide consisting of the amino acid sequence shown by SEQ ID NO:6 or SEQ ID NO:8 can be cloned by extracting total RNA from the expression site thereof (for example, heart, ovary, colon and the like), preparing cDNA from the mRNA, then performing a PCR using an appropriate primer. The polynucleotide that encodes an equivalent to a polypeptide consisting of the amino acid sequence shown by SEQ ID NO:6 or SEQ ID NO:8 can be prepared by inducing a mutation in a polynucleotide cloned as described above. As examples of the method of mutagenesis, the synthetic oligonucleotide site-directed mutagenesis (gapped duplex) method, a method of randomly inducing point mutations (for example, treatment with nitrous acid or sulfurous acid), the cassette mutation method, the linker scanning method, the mismatch primer method and the like can be mentioned.

A polypeptide of the present invention can also be prepared by a method known per se. For example, a polynucleotide of the present invention prepared as described above is inserted into an expression vector, the recombination vector obtained is introduced into an appropriate host cell to obtain a transformant, after which the transformant is cultured to produce a polypeptide of the present invention, which is then recovered. The present invention also provides such a recombination vector and a transformant incorporating the vector.

The expression vector is not subject to limitation, as long as it is capable of expressing the gene that encodes a polypeptide of the present invention, and of producing these polypeptides in various host cells such as prokaryotic cells and/or eukaryotic cells. For example, plasmid vectors, viral vectors (for example, adenovirus, retrovirus) and the like can be mentioned.

When a bacterium, particularly *Escherichia coli*, is used as the host cell, the expression vector is generally composed of at least a promoter-operator region, an initiation codon, a DNA that encodes a polypeptide of the present invention, a stop codon, a terminator region and a replicable unit.

When a yeast, animal cell or insect cell is used as the host, the expression vector preferably comprises at least a promoter, an initiation codon, a DNA that encodes a polypeptide of the present invention, and a stop codon. The expression vector may also comprise an enhancer sequence, the 5'-terminal and 3'-terminal non-translated regions of the gene that encodes a polypeptide of the present invention, a splicing junction, a polyadenylation site, a selection marker region or a replicable unit and the like. The expression vector may also comprise a commonly used gene amplification gene (marker) according to the purpose of use.

The promoter-operator region for expressing a polypeptide of the present invention in a bacterium comprises a promoter, an operator and a Shine-Dalgarno (SD) sequence (for example, AAGG and the like). For example, when the host is a bacterium of the genus *Escherichia*, those comprising the Trp promoter, lac promoter, recA promoter, λPL promoter, lpp promoter, tac promoter and the like can be mentioned as the promoter-operator region. As the promoter used to express a polypeptide of the present invention in yeast, the PH05 promoter, PGK promoter, GAP promoter, and ADH promoter can be mentioned; when the host is a bacterium of the genus *Bacillus*, the SL01 promoter, SP02 promoter, penP promoter and the like can be mentioned. When the host is a eukaryotic cell such as a mammalian cell, the SV40-derived promoter, retrovirus promoter, heat shock promoter and the like can be mentioned.

Regarding the terminator region, replicable unit, enhancer sequence, polyadenylation site, and splicing junction site, those known per se can be used.

As the selection marker, one known per se can be used. For example, genes for resistance to antibiotics such as tetracycline, ampicillin, and kanamycin can be mentioned.

As examples of the gene amplification gene, the dihydrofolate reductase (DHFR) gene, thymidine kinase gene, neomycin resistance gene, glutamic acid synthase gene, adenosine deaminase gene, ornithine decarboxylase gene, hygromycin-B-phosphotransferase gene, aspartate transcarbamylase gene and the like can be mentioned.

The recombination vector of the present invention can be prepared by continuously and cyclically joining at least the above-described promoter, initiation codon, DNA that encodes a polypeptide of the present invention, stop codon and terminator region to an appropriate replicable unit. In this operation, an appropriate DNA fragment (for example, linker, other restriction endonuclease cleavage site and the like) can be used by a conventional method such as digestion with restriction enzyme or ligation using T4 DNA ligase if desired.

The transformant of the present invention can be prepared by introducing the above-described recombination vector into a host cell.

The host cell used to prepare a transformant is not subject to limitation, as long as it matches with the aforementioned expression vector and is transformable; various cells in common use in the technical field of the present invention, such as natural cells or an artificially established line of recombinant cells (for example, bacteria (bacteria of the genus *Escherichia*, bacteria of the genus *Bacillus*), yeasts (the genus *Saccharomyces*, the genus *Pichia* and the like), animal cells or insect cells (preferably Sf9) and the like, can be utilized.

Introduction of the expression vector into a host cell can be performed using a method known per se. For example, transformation can be performed by the method of Graham (Virology, Vol. 52, p. 456, 1973) in the case of animal cells, and by the method of Summers et al. (Mol. Cell. Biol., Vol. 3, p. 2156-2165, 1983) in the case of insect cells.

A polypeptide of the present invention can be produced by culturing a transformant comprising an expression vector, prepared as described above, using a nutrient medium.

The nutrient medium preferably contains a carbon source and an inorganic nitrogen source or organic nitrogen source, which are required for the growth of the transformant. As examples of the carbon source, glucose, dextran, soluble starch, sucrose and the like can be mentioned; as examples of the inorganic nitrogen source or organic nitrogen source, ammonium salts, nitrates, amino acids, corn steep liquor, peptone, casein, meat extract, soybean cake, potato extract and the like can be mentioned. If desired, other nutrients [for example, inorganic salts (for example, calcium chloride, sodium dihydrogen phosphate, magnesium chloride), vitamins, antibiotics (for example, tetracycline, neomycin, ampicillin, kanamycin and the like)] may be contained.

Cultivation of the transformant is performed by a method known per se. Culturing conditions, for example, temperature, pH of the medium, and cultivation time are chosen as appropriate so that a polypeptide of the present invention is produced in a large amount.

Specific examples of the medium and culturing conditions used according to the host cell are given below, which, however, are not to be construed as limiting the present invention.

When the host is an animal cell, as examples of the medium, an MEM medium comprising about 5 to 20% fetal calf serum (Science, Vol. 122, p. 501, 1952), DMEM medium (Virology, Vol. 8, p. 396, 1959), RPMI1640 medium (J. Am. Med. Assoc., Vol. 199, p. 519, 1967), 199 medium (Proc. Soc. Exp. Biol. Med., Vol. 73, p. 1, 1950) and the like can be used. The pH of the medium is preferably about 6 to 8, cultivation is normally performed at about 30 to 40° C. for about 15 to 72 hours, and the culture may be aerated or agitated as necessary.

When the host is an insect cell, as examples of the medium, Grace's medium comprising fetal calf serum (Proc. Natl. Acad. Sci. USA, Vol. 82, p. 8404, 1985) and the like can be mentioned, and the pH thereof is preferably about 5 to 8. Cultivation is normally performed at about 20 to 40° C. for 15 to 100 hours, and the culture may be aerated or agitated as necessary.

When the host is a bacterium, actynomecete, yeast, or filamentous fungus, a liquid medium comprising the above-described nutrient sources, for example, is appropriate. Preferably, the medium has a pH of 5 to 8.

When the host is *E. coli*, as examples of the preferable medium, LB medium, M9 medium (Miller et al., Exp. Mol. Genet, Cold Spring Harbor Laboratory, p. 431, 1972) and the like can be mentioned. In this case, cultivation can be performed normally at 14 to 43° C. for about 3 to 24 hours, while the culture is aerated or agitated as necessary.

When the host is a bacterium of the genus *Bacillus*, cultivation can be performed normally at 30 to 40° C. for about 16 to 96 hours, while the culture is aerated or agitated as necessary.

When the host is yeast, as examples of the medium, Burkholder's minimal medium (Bostian, Proc. Natl. Acad. Sci. USA, Vol. 77, p. 4505, 1980) can be mentioned, and the pH of the medium is desirably 5 to 8. Cultivation is normally performed at about 20 to 35° C. for about 14 to 144 hours, and the culture may be aerated or agitated as necessary.

A polypeptide of the present invention can be recovered, preferably isolated and purified, from a cultured transformant as described above.

As examples of the methods of isolation and purification, methods based on differences in solubility, such as salting-out and solvent precipitation; methods based on differences in molecular weight, such as dialysis, ultrafiltration, gel filtration, and sodium dodecyl sulfate-polyacrylamide gel electrophoresis; methods based on differences in electric charge, such as ion exchange chromatography and hydroxylapatite chromatography; methods based on specific affinity, such as affinity chromatography; methods based on differences in hydrophobicity, such as reverse phase high performance liquid chromatography; methods based on differences in isoelectric point, such as isoelectric focusing; and the like can be mentioned.

By allowing the transformant to produce a polypeptide with a tag (for example, histidine tag, Flag tag), and using a substance having affinity for the tag (for example, $Ni^{2+}$ resin, antibody specific for the tag), a polypeptide of the present invention can be isolated and purified more conveniently.

Furthermore, a polypeptide of the present invention can be synthesized using a cell-free system. In the synthesis of a polypeptide of the present invention using a cell-free system, for example, *Escherichia coli*, rabbit reticulocytes, wheat germ extract and the like can be used. A polypeptide of the present invention can be prepared by an organochemical method known per se, such as the solid phase synthesis method or the liquid phase synthesis method.

2.2. Cleaving Method

A polypeptide of the present invention can be obtained by contacting DANCE with a DANCE-specific protease to cleave the DANCE. The present invention still also provides such a method of cleavage.

The contact of DANCE with the DANCE-specific protease in this method may be in any mode, as long as the amino acid sequence shown by SEQ ID NO:2 is cleaved between the 77th amino acid and the 78th amino acid in the amino acid sequence; as an example of the mode of contact to achieve this cleavage, cultivation of cells expressing both DANCE and the DANCE-specific protease can be mentioned. Cultivation of such cells can be performed in accordance with the above-described cultivation of a transformant.

The cells expressing both DANCE and the DANCE-specific protease are not subject to limitation, as long as these two proteins are expressed. Such cells can be prepared by, for example, introduction of a DANCE-specific protease expression vector into DANCE expression cells (for example, cells that naturally express DANCE, or cells becoming capable of expressing DANCE by gene manipulation), introduction of a DANCE expression vector into DANCE-specific protease expression cells, introduction of a DANCE expression vector and a DANCE-specific protease expression vector into optionally chosen cells, and the like.

To enhance the expression, a DANCE and/or DANCE-specific protease expression vector may be introduced into DANCE and/or DANCE-specific protease expression cells, respectively.

The DANCE expression cells may be primary culture cells or of a cell line. The major DANCE expression site is not subject to limitation; for example, heart, kidney, pancreas, testis, ovary, small intestine, colon, arteries, lungs, uterus, and skin are known to serve as the DANCE expression site, cells derived from tissues corresponding to these expression sites per se, or cells derived therefrom, can be used as DANCE expression cells. Primary culture cells and a cell line can be prepared by a method known per se [see, for example, Current Protocols in Cell Biology, John Wiley & Sons, Inc. (2001); Separation and Cultivation of Functional Cells, Maruzen Shoten (1987)].

The DANCE-specific protease expression cells may also be primary culture cells or of a cell line. For example, because the expression of a DANCE-specific protease has been confirmed in cells such as skin fibroblasts and 293T cells, and tissues such as lungs and skin, these cells per se, or cells derived from these tissues, or cells derived therefrom, can be used as the DANCE-specific protease expression cells. Cells found to have DANCE cleavage activity as a result of an evaluation to determine whether or not a particular cell has DANCE cleavage activity can likewise be used as the DANCE-specific protease expression cells. The present invention also provides a method of identifying such DANCE-specific protease expression cells using animal cells (for example, mammalian cells such as human cells).

Regarding the kind of cells used in this method of cleavage, cells of the same kind as the host used to prepare the above-described transformant can be used, with preference given to insect cells and animal cells (for example, mammalian cells).

A DANCE expression vector can be prepared in the same manner as the vector expressing a polypeptide of the present invention.

A DANCE-specific protease expression vector can be prepared by a method described with respect to the screening methods for a DANCE-specific protease described below. The DANCE-specific protease expression vector may be a mixture with a vector to express a gene product other than a DANCE-specific protease, obtained from a transformant wherein the DANCE-specific expression vector has been concentrated, in the expression screening described below.

As another mode of the contact in this method of cleavage, addition of DANCE to a fraction containing a DANCE-specific protease can be mentioned. The fraction containing a DANCE-specific protease is not subject to limitation, as long as it has DANCE cleavage activity; for example, culture supernatant of DANCE-specific protease expression cells, extract of the cells, extract of a tissue showing the expression of a DANCE-specific protease, crudely purified liquid from the culture supernatant or extract and the like can be mentioned. If a DANCE-specific protease has been isolated and purified, cleavage of DANCE becomes possible by mixing the fraction containing DANCE or an isolated DANCE and an isolated DANCE-specific protease.

Cleavage of DANCE with a DANCE-specific protease can be confirmed by an immunological technique (for example, immunoprecipitatation, Western blotting) using an anti-DANCE antibody and the like.

This method of cleavage is useful not only for the preparation of a polypeptide of the present invention, but also as an index in a screening method of the present invention.

3. Antibodies Against N-Terminal Side and C-Terminal Side Polypeptides Resulting from Cleavage of DANCE The present invention also provides an antibody against an N-terminal side polypeptide resulting from the cleavage of DANCE with a DANCE-specific protease (i.e., a polypeptide consisting of the amino acid sequence shown by SEQ ID NO:6, or an equivalent thereto), and an antibody against a C-terminal side polypeptide (i.e., a polypeptide consisting of the amino acid sequence shown by SEQ ID NO:8, or an equivalent thereto).

As the antigen used to prepare an antibody of the present invention, a polypeptide consisting of the amino acid sequence shown by SEQ ID NO:6 or SEQ ID NO:8 or an equivalent thereto, or a partial peptide thereof can be used. The partial peptide is not subject to limitation, as long as it has antigenicity, and it can, for example, be a peptide consisting of at least 6, preferably at least 8, more preferably at least 10, still more preferably at least 15 or more, continuous amino acids selected from the amino acid sequence shown by SEQ ID NO:6 or SEQ ID NO:8, or substantially the same amino acid sequence as the amino acid sequence shown by SEQ ID NO:6 or SEQ ID NO:8.

The antibody of the present invention may be a polyclonal antibody or monoclonal antibody, and can be prepared by a well-known immunological technique. This antibody is not only a complete antibody molecule, but also any fragment as long as it has an antigen-binding site (CDR) for the protein of the present invention, and is exemplified by Fab, F(ab')$_2$, ScFv, minibody, and the like.

For example, a polyclonal antibody can be obtained by giving the antigen [may be prepared as a complex cross-linked with a carrier protein such as bovine serum albumin or KLH (Keyhole Limpet Hemocyanin), if necessary], along with a commercially available adjuvant (e.g., complete or incomplete Freund's adjuvant), to an animal by subcutaneous or intraperitoneal administration about 2 to 4 times at intervals of 2 to 3 weeks (the antibody titer of serum separated from drawn blood determined by a commonly known antigen-antibody reaction, and its elevation confirmed in advance), collecting whole blood about 3 to about 10 days after final immunization, and purifying the antiserum. Animals to be administered with the antigen include mammals such as rats, mice, rabbits, goat, guinea pigs and hamsters.

A monoclonal antibody can also be prepared by a cell fusion method. For example, a mouse is given this factor, along with a commercially available adjuvant, 2 to 4 times by subcutaneous or intraperitoneal administration, its spleen or lymph node is collected about 3 days after final administration, and leukocytes are separated. These leukocytes are fused with myeloma cells (e.g., NS-1, P3X63Ag8, etc.) to yield a hybridoma that produces a monoclonal antibody against this antigen. The cell fusion may be achieved by the PEG method or the voltage pulsation method. A hybridoma that produces the desired monoclonal antibody can be selected by detecting in the culture supernatant an antibody that specifically binds to an antigen using well-known EIA, RIA, or the like. Cultivation of a hybridoma that produces monoclonal antibody can be conducted in vitro, or in vivo in mice or rats, preferably in ascites fluid of mouse, and the resulting antibody can be obtained from a hybridoma culture supernatant or animal ascites fluid, respectively.

Furthermore, the antibody of the present invention may be a chimeric antibody, a humanized antibody, a human antibody, or a chimeric antibody. A chimeric antibody can be prepared with reference to, for example, "Jikken Igaku (extra issue), Vol. 6, No. 10, 1988", Japanese Patent Examined Publication No. HEI-3-73280 and the like; a humanized antibody can be prepared with reference to, for example, Japanese Patent Kohyo Publication No. HEI-4-506458, Japanese Patent Unexamined Publication No. SHO-62-296890 and the like; a human antibody can be prepared with reference to, for example, "Nature Genetics, Vol. 15, p. 146-156, 1997", "Nature Genetics, Vol. 7, p. 13-21, 1994", Japanese Patent Kohyo Publication No. HEI-4-504365, International patent Publication WO94/25585, "Nikkei Science, June issue, pages 40 to 50, 1995", "Nature, Vol. 368, p. 856-859, 1994", Japanese Patent Kohyo Publication No. HEI-6-500233 and the like.

The antibody of the present invention is capable of specifically detecting or inhibiting one of the polypeptides of the present invention, and is therefore useful, for, for example, performing a screening method of the present invention, and as a regulator of the formation of elastic fibers and as a research and diagnostic reagent for DANCE.

4. Method of Measuring the Amount of DANCE Cleaved and Cleavage Activity, and a Kit Therefor The present invention provides a method comprising measuring the amount of DANCE cleaved and/or cleavage activity with a DANCE-specific protease, particularly a method comprising measuring the amount of DANCE cleaved with a DANCE-specific protease in a biological sample from an animal, and a kit enabling the measurement.

When a biological sample from an animal is used in this method, the animal used is not subject to limitation, as long as it is a warm-blooded animal, and the animal can, for example, be a mammal. The mammal is not subject to limitation; as examples of the mammal, human, bovine, sheep, swine, goat, monkey, rabbit, rat, hamster, guinea pig, and mouse can be mentioned.

The biological sample is not subject to limitation, as long as it is collectable from the above-described animal. As examples of the biological sample, those collected from tissues such as the skin, arteries, lungs, and uterus can be mentioned.

The amount of DANCE cleaved can be measured by a method known per se. For example, the amount of DANCE cleaved can be measured by an immunological technique using an anti-DANCE antibody (for example, Western blotting). In this case, not only the above-described antibody of the present invention, but also an optionally chosen anti-DANCE antibody (for example, an antibody prepared using a partial peptide striding the DANCE cleavage site as the antigen) can be used. Such an antibody can be prepared in accordance with the above-described method of preparing an antibody.

When using an anti-DANCE antibody for measuring the amount of DANCE cleaved, the amount of DANCE cleaved can be measured by, for example, using a labeled anti-DANCE antibody, or using combination of an anti-DANCE antibody and a labeled secondary antibody.

As the label for the anti-DANCE antibody, enzymes such as alkaline phosphatase, glucose oxidase, peroxidase, and β-galactosidase, fluorescent substances and the like can be mentioned. Binding of these labels and an anti-DANCE antibody can be achieved by a method known per se, for example, the glutaraldehyde method, the maleimide method and the like.

When the label is an enzyme, an appropriate substrate is chosen according to the enzyme selected. For example, when alkaline phosphatase is selected as the enzyme, p-nitrophenyl phosphate (PNPP) and the like are used; in this case, o-phenylenediamine (OPD), tetramethylbenzidine (TMB) and the like are used as the color developing agent. Regarding the washing solution, reaction stopper solution, and substrate solvent, conventionally known ones can be used as appropriate without limitation according to the enzyme selected.

DANCE cleavage activity can be measured by, for example, constructing and using a system that produces fluorescence only when cleavage has occurred between a fluorescent molecule bound to one end of a polypeptide having the DANCE cleavage site and a quencher bound to the other end. Construction of such a system can be achieved by a method known per se.

The fluorescent molecule used for measuring DANCE cleavage activity is not subject to limitation, as long as it enables an evaluation of DANCE cleavage activity; for example, FITC, 6-FAM, HEX, TET, EDANS, Alexa (registered trademark) Fluor (Invitrogen) and the like can be mentioned.

The quencher used for measuring DANCE cleavage activity is not subject to limitation, as long as it enables an evaluation of DANCE cleavage activity; for example, TAMRA, Dabcyl, Eclipse, QSY quencher pigment (Invitrogen) and the like can be mentioned.

The measurement method of the present invention is useful, for example, for performing a screening method of the present invention, and for enabling a diagnosis of the status of the formation of elastic fibers, particularly analysis at molecular levels.

The present invention also relates to a kit enabling measurements of the amount of DANCE cleaved and/or cleavage activity.

In addition to the above-described anti-DANCE antibody, the kit of the present invention, which enables measurements of the amount of DANCE cleaved, can comprise DANCE, a secondary antibody, a substrate for labeled enzyme, a reagent necessary for the treatment of a biological sample and the like. This kit can also comprise one or both of the polypeptides resulting from the cleavage of DANCE (i.e., the polypeptides of the present invention) as controls. This kit may further comprise an instruction manual bearing the statement that the amount of DANCE cleaved can serve as an index of the formation of elastic fibers.

The kit of the present invention, which enables measurements of DANCE cleavage activity, can comprise DANCE, a fluorescent molecule, a quencher and the like. This kit can also comprise the above-described DANCE mutant as control. This kit may further comprise an instruction manual bearing the statement that DANCE cleavage activity can serve as an index of the formation of elastic fibers.

The measurement kit of the present invention is useful for providing a means enabling convenient measurements of the amount of DANCE cleaved and/or cleavage activity.

5. DANCE Mutant and a Polynucleotide that Encodes the Same

The present invention also provides a DANCE mutant wherein an amino acid mutation has been introduced in the DANCE cleavage site with a DANCE-specific protease to confer resistance to the protease, or a polynucleotide that encodes the polypeptide.

The DANCE mutant of the present invention is characterized in that the protease cleavage site (Arg-Gly: corresponding to the 77th to 78th amino acids in the amino acid sequence shown by SEQ ID NO:2, and the 54th to 55th amino acids in the amino acid sequence shown by SEQ ID NO:4) or an amino acids in the vicinity thereof (for example, the 70th to 85th, preferably the 72nd to 83rd, more preferably the 74th to 81st, still more preferably the 76th to 79th, amino acids, in the amino acid sequence shown by SEQ ID NO:2, or the 47th to 62nd, preferably the 49th to 60th, more preferably the 51st to 59th, still more preferably the 53rd to 56th, amino acids in the amino acid sequence shown by SEQ ID NO:4) has been mutated (for example, deleted, added, substituted) to exhibit resistance to a DANCE-specific protease, in the amino acid sequence shown by SEQ ID NO:2 or SEQ ID NO:4, or in substantially the same amino acid sequence as the amino acid sequence shown by SEQ ID NO:2 or SEQ ID NO:4. As used herein, "substantially the same" has the same definition as described above.

"Exhibit resistance to DANCE-specific protease" means that DANCE cleavage capability of a DANCE-specific protease decreases after the mutation (for example, a reduction of not more than 75%, preferably not more than 50%), and the extent of the reduction in cleavage capability is not subject to limitation. Whether or not the DANCE mutant exhibits resistance to a DANCE-specific protease can be confirmed by cleaving normal DANCE and the DANCE mutant by the above-described method of cleavage, then measuring and comparing the amounts of normal DANCE and DANCE mutant cleaved.

As examples of the DANCE mutant of the present invention, a polypeptide consisting of an amino acid sequence resulting from the substitution of the 77th arginine with alanine in the amino acid sequence shown by SEQ ID NO:2, or in substantially the same amino acid sequence as the amino acid sequence shown by SEQ ID NO:2, and a polypeptide consisting of an amino acid sequence resulting from the substitution of the 54th arginine with alanine in the amino acid sequence shown by SEQ ID NO:4, or in substantially the same amino acid sequence as the amino acid sequence shown by SEQ ID NO:4, can be mentioned.

The present invention also provides a recombination vector comprising the DANCE mutant of the present invention, and a transformant comprising the vector.

The DANCE mutant of the present invention and a polynucleotide that encodes the mutant are useful as, for example, negative controls in a screening method of the present invention, and as regulators of the formation of elastic fibers (for example, for forming elastic fibers) and research reagents.

6. DANCE Complexes

6.1. DANCE Complex Comprising at Least Two DANCEs (Complex I)

The present invention provides a DANCE complex comprising at least two DANCEs (complex I).

This complex I may further comprise lysyl oxidase and/or LTBP2. Lysyl oxidase and/or LTBP2 can be prepared as described below.

This complex I may also further comprise integrin and/or lysyl oxidase-like-1. As the integrin that can be used in the present invention, various types of integrin can be mentioned, with preference given to $\alpha_5\beta_1$, $\alpha_{IIb}\beta_3$, all $\alpha_v\beta$, and $\alpha_9\beta_1$. These types of integrin and lysyl oxidase-like-1, and the expression sites thereof are publicly known, and cloning of their genes and preparation of expression cells can be performed by methods known per se.

Preferably, this complex I comprises at least two kinds of DANCE which are distinguishable forms. As used herein, "distinguishable form" means that a difference exists between the at least two DANCEs, and that the difference is detectable. As examples of the combination of distinguishable form of DANCE, a combination of labeled DANCE and non-labeled DANCE and a combination of two different kinds of labeled DANCE can be mentioned.

The labeling of DANCE is not subject to limitation, as long as the labeled DANCE is distinguishable from the non-labeled DANCE or DANCE with a different kind of label; for example, labeling with an epitope and labeling with a radioisotope (for example, $^{35}$S) can be mentioned.

As examples of the epitope used to label DANCE, glutathione-5-transferase (GST), maltose-binding protein (MBP), influenza hemagglutinin (HA), thioredoxin (Trx), histidine (His) tag, FLAG tag, Myc tag and the like can be mentioned.

When the complex I of the present invention further comprises one or more selected from among lysyl oxidase, LTBP2, integrin, and lysyl oxidase-like-1, they may be labeled or not.

Epitope-labeled DANCE can be prepared by a method known per se. For example, DANCE labeled with an epitope can be prepared by appropriately joining a DANCE-encoding polynucleotide to the nucleotide that encodes the epitope to yield a DNA construct, and expressing this DNA construct in host cells. On the other hand, DANCE labeled with a radioisotope (for example, $^{35}$S) can be prepared by culturing DANCE expression cells using a medium containing the radioisotope.

The present invention also provides a method of preparing the above-described complex I. The method of preparing the complex I comprises contacting at least two DANCEs to form a complex.

When preparing the complex I, lysyl oxidase and/or LTBP2 may further be contacted. Furthermore, integrin and/or lysyl oxidase-like-1 can also be contacted.

Formation of the complex I can be achieved by preparing DANCE (i.e., association inevitable to the preparation of DANCE), or contacting at least two separately prepared kinds of DANCE (labeled DANCE-non-labeled DANCE, and two different kinds of labeled DANCE).

More specifically, formation of the complex I can be achieved by contacting isolated DANCE with isolated DANCE (for example, distinguishable form), and introducing a DANCE expression vector into DANCE expression cells (including in vitro and in vivo) and the like.

The complex I, particularly a complex comprising at least two kinds of DANCE which are distinguishable form, and a method of preparing the complex are useful as an index in the screening method for a substance capable of regulating the formation of a DANCE complex, and as a regulator of the formation of elastic fibers and as a research reagent for DANCE.

6.2. DANCE Complex Comprising at Least One DANCE and Lysyl Oxidase (Complex II)

The present invention provides a DANCE complex comprising at least one DANCE and lysyl oxidase (complex II).

This complex II may further comprise DANCE (for example, distinguishable form of DANCE) and/or LTBP2. This complex II may further comprise integrin and/or lysyl oxidase-like-1. Each of LTBP2, integrin, and lysyl oxidase-like-1 may be labeled as described above or not.

The present invention also provides a method of preparing the above-described complex II. The method of preparing the complex II comprises contacting at least one DANCE with lysyl oxidase to form a complex.

When preparing the complex II, DANCE (for example, distinguishable form of DANCE) and/or LTBP2 may further be contacted. Furthermore, integrin and/or lysyl oxidase-like-1 can be contacted.

Formation of the complex II can be achieved by, for example, contacting unlabeled DANCE with unlabeled lysyl oxidase, contacting unlabeled DANCE with labeled lysyl oxidase, contacting labeled DANCE with unlabeled lysyl oxidase, contacting DANCE with lysyl oxidase wherein DANCE and lysyl oxidase have the same kind of label respectively, or contacting DANCE with lysyl oxidase wherein DANCE and lysyl oxidase have different labels respectively.

More specifically, formation of the complex II can be achieved by contacting isolated DANCE with isolated lysyl oxidase, introducing a lysyl oxidase expression vector into DANCE expression cells, and introducing a DANCE expression vector into lysyl oxidase expression cells (including in vitro and in vivo) and the like.

Lysyl oxidase and the expression site thereof are publicly known. Therefore, a lysyl oxidase expression vector, and lysyl oxidase expression cells (for example, primary culture cells, a cell line) can be prepared by methods known per se. For example, because it has been confirmed that lysyl oxidase is expressed in cells such as those of vascular smooth muscle, skin, fibroblasts and the likes, and tissues such as the arteries, skin, lungs, and uterus, the lysyl oxidase gene can be cloned, and lysyl oxidase expression cells can be prepared, from these cells and tissues.

The complex II, and a method of preparing the complex are useful as an index in the screening method for a substance capable of regulating the formation of a DANCE complex, as a regulator of the formation of elastic fibers, and as a research reagent for DANCE.

6.3. DANCE Complex Comprising at Least One DANCE and LTBP2 (Complex III)

The present invention provides a DANCE complex comprising at least one DANCE and LTBP2 (complex III).

This complex III may further comprise DANCE (for example, distinguishable form of DANCE) and/or lysyl oxidase. This complex III may still further comprise integrin and/or lysyl oxidase-like-1. Lysyl oxidase, integrin, and lysyl oxidase-like-1 may be labeled as described above, or not.

The present invention also provides a method of preparing the above-described complex III. The method of preparing the complex III comprises contacting at least one DANCE with LTBP2 to form a complex.

When preparing the complex III, DANCE (for example, distinguishable form of DANCE) and/or lysyl oxidase may further be contacted. Furthermore, integrin and/or lysyl oxidase-like-1 can also be contacted.

Formation of the complex III can be achieved by, for example, contacting unlabeled DANCE with unlabeled LTBP2, contacting unlabeled DANCE with labeled LTBP2, contacting labeled DANCE with unlabeled LTBP2, contacting DANCE with LTBP2 wherein DANCE and LTBP2 have the same kind of label respectively, or contacting DANCE with LTBP2 wherein DANCE and LTBP2 have different labels respectively.

More specifically, formation of the complex III can be achieved by contacting isolated DANCE with isolated LTBP2, introducing an LTBP2 expression vector into DANCE expression cells, and introducing a DANCE expression vector into LTBP2 expression cells (including in vitro and in vivo) and the like.

LTBP2 and the expression site thereof are publicly known. Therefore, an LTBP2 expression vector and LTBP2 expression cells (for example, primary culture cells, a cell line) can be prepared by methods known per se. For example, since it has been confirmed that LTBP2 is expressed in cells such as vascular smooth muscle cells and skin fibroblasts, and tissues such as arteries, skin, lungs, and uterus, the LTBP2 gene can be cloned, and LTBP2 expression cells can be prepared, from these cells and tissues.

The complex III and a method of preparing the complex are useful as an index in the screening method for a substance capable of regulating the formation of a DANCE complex, as a regulator of the formation of elastic fibers, and as a research reagent for DANCE.

7. Screening Methods

The present invention provides various screening methods. The screening methods of the present invention are roughly divided into screening methods for a substance capable of regulating the activity of a DANCE-specific protease (screening methods I and II), screening methods for a substance capable of regulating the formation of a DANCE complex (screening methods III to V), and a screening method for a DANCE-specific protease (screening method VI). Hereinafter, the individual screening methods are described in detail.

7.1. Screening Method for a Substance Capable of Regulating the Activity of a DANCE-Specific Protease (In Vitro) (Screening Method I)

The screening method I is not subject to limitation, as long as it enables an evaluation of the activity of a DANCE-specific protease without using an animal, and it comprises, for example, the following steps (a), (b) and (c):

(a) contacting a test substance with the DANCE-specific protease;

(b) measuring the activity of the DANCE-specific protease resulting from the step (a) above, and comparing the activity with the activity of the DANCE-specific protease obtained when the test substance is not contacted;

(c) selecting a test substance that regulates the activity of the DANCE-specific protease on the basis of the results of the comparison in (b) above.

Note that the substances capable of regulating the activity of a DANCE-specific protease include not only what are called agonists and antagonists of the DANCE-specific protease, but also substances capable of varying the amount of the DANCE-specific protease expressed, in view of the nature of this screening method I.

In the step (a), the test substance may be any known compound or new compound; for example, nucleic acids, saccharides, lipids, proteins, peptides, organic small compounds, compound libraries prepared using combinatorial chemistry technique, random peptide libraries prepared by the solid phase synthesis or phage display method, or natural components derived from microorganisms, animals, plants, marine organisms and the like, and the like can be mentioned.

The contact of the test substance with a DANCE-specific protease is the same as the contact mentioned in "2.2. Cleaving method".

In the step (b), the activity of the DANCE-specific protease can be evaluated on the basis of the amount of DANCE cleaved and/or cleavage activity. For example, the amount of DANCE cleaved and cleavage activity can be measured by methods mentioned in "4. Method of measuring the amount of DANCE cleaved and cleavage activity, and a kit therefor".

A comparison of the amount of DANCE cleaved and/or cleavage activity can be performed on the basis of the presence or absence of a significant difference in the amount of DANCE cleaved and/or cleavage activity in the presence and absence of a test substance. Although the amount of DANCE cleaved and/or cleavage activity in the absence of the test substance may be measured previously or simultaneously relative to the measurement of the amount of DANCE cleaved and/or cleavage activity in the presence of the test substance, it is preferable to perform a simultaneous measurement from the viewpoint of experimental accuracy and reproducibility.

Subsequently, in the step (c), a test substance that regulates the activity of the DANCE-specific protease is selected. The thus-selected test substance is useful as a regulator of the formation of elastic fibers or as a research reagent. For example, a substance that inhibits the activity of a DANCE-specific protease can be useful for maintaining the formation of elastic fibers.

7.2. Screening Method for Substance Capable of Regulating the Activity of DANCE-Specific Protease (In Vivo) (Screening Method II)

The screening method II is not subject to limitation, as long as it enables an evaluation of the activity of a DANCE-specific protease, and it comprises, for example, the following steps (a), (b) and (c):

(a) administering a test substance to an animal;

(b) measuring the activity of the DANCE-specific protease resulting from the step (a) above, and comparing the activity with the activity of the DANCE-specific protease obtained without administering the test substance;

(c) selecting a test substance that regulates the activity of the DANCE-specific protease on the basis of the results of the comparison in (b) above.

Note that the substances capable of regulating the activity of a DANCE-specific protease include not only what are called agonists and antagonists of the DANCE-specific protease, but also substances capable of varying the amount of DANCE-specific protease expressed, in view of the nature of this screening method II.

In the step (a), a test substance similar to that used in the screening method I can be used.

Administration of the test substance to the animal is performed by a method known per se. Dosage, frequency and duration of administration can be established at optionally chosen levels. the animals to which this method is applicable are the same as the animals mentioned in "4. Method of measuring the amount of DANCE cleaved, and a kit therefor".

In the step (b), the activity of the DANCE-specific protease can, for example, be evaluated on the basis of the amount of DANCE cleaved in a biological sample after the biological sample is collected from the subject animal. The biological sample and the method of measuring the amount of DANCE cleaved are the same as those mentioned in "4. Methods of measuring the amount of DANCE cleaved and cleavage activity, and a kit therefor".

A comparison of the amount of DANCE cleaved can be performed on the basis of the presence or absence of a significant difference in the amount of DANCE cleaved with and without administration of the test substance. Although the amount of DANCE cleaved obtained without administration of the test substance may be measured previously or simultaneously relative to the measurement of the amount of DANCE cleaved at the time of administration of the test substance, it is preferable to perform a simultaneous measurement, from the viewpoint of experimental accuracy and reproducibility.

Subsequently, in the step (c), a test substance that regulates the activity of the DANCE-specific protease is selected. The thus-selected test substance is useful as a regulator of the formation of elastic fibers or as a research reagent. For example, a substance that inhibits the activity of a DANCE-specific protease can be useful for maintaining the formation of elastic fibers.

7.3. Screening Method for Substance Capable of Regulating the Formation of DANCE Complex Comprising at Least Two DANCEs (Complex I) (Screening Method III)

The screening method III is not subject to limitation, as long as it enables an evaluation of the formation of the complex I, and it comprises, for example, the following steps (a), (b) and (c):

(a) contacting at least two DANCEs in the presence of a test substance;
(b) measuring the amount of DANCE complex resulting from the step (a) above, and comparing the amount with the amount of DANCE complex obtained in the absence of the test substance;
(c) selecting a test substance that regulates the formation of the DANCE complex on the basis of the results of the comparison in (b) above.

In the step (a), a test substance similar to that used in the screening method I can be used.

The contact of at least two DANCEs is the same as the contact mentioned in "6.1. DANCE complex comprising at least two DANCEs (complex I)". In this screening method III, it is preferable to use distinguishable form of DANCE.

In the step (b), the amount of the complex I can be measured by a combination of an immunoprecipitation method (see, for example, Example 6) and densitometry, an interaction analytical method such as surface plasmon resonance, a method based on ELISA, and the like.

A comparison of the amount of the complex I can be performed on the basis of the presence or absence of a significant difference in the amount of the complex I in the presence and absence of the test substance. Although the amount of the complex I in the absence of the test substance may be measured previously or simultaneously relative to the measurement of the amount of the complex I in the presence of the test substance, it is preferable to perform a simultaneous measurement, from the viewpoint of experimental accuracy and reproducibility.

Subsequently, in the step (c), a test substance that regulates the formation of the complex I is selected. The thus-selected test substance is useful as a regulator of the formation of elastic fibers or as a research reagent. For example, a substance that promotes the formation of the complex I can be useful for the formation of elastic fibers.

7.4. Screening Method for Substance Capable of Regulating the Formation of DANCE Complex Comprising at Least One DANCE and Lysyl Oxidase (Complex II) (Screening Method IV)

The screening method IV is not subject to limitation, as long as it enables an evaluation of the formation of the complex II, and it comprises, for example, the following steps (a), (b) and (c):

(a) contacting at least one DANCE with lysyl oxidase in the presence of a test substance;
(b) measuring the amount of the DANCE complex resulting from the step (a) above, and comparing the amount with the amount of the DANCE complex obtained in the absence of the test substance;
(c) selecting a test substance that regulates the formation of the DANCE complex on the basis of the results of the comparison in (b) above.

In the step (a), a test substance similar to that used in the screening method I can be used.

The contact of at least one DANCE and lysyl oxidase is the same as the contact mentioned in "6.2. DANCE complex comprising at least one DANCE and lysyl oxidase (complex I)".

In the step (b), the amount of the complex II can be measured by a combination of an immunoprecipitation method (see, for example, Example 7) and densitometry, an interaction analytical method such as surface plasmon resonance, a method based on ELISA, and the like.

A comparison of the amount of the complex II can be performed on the basis of the presence or absence of a significant difference in the amount of the complex II in the presence and absence of the test substance. Although the amount of the complex II in the absence of the test substance may be measured previously or simultaneously relative to the measurement of the amount of the complex II in the presence of the test substance, it is preferable to perform a simultaneous measurement, from the viewpoint of experimental accuracy and reproducibility.

Subsequently, in the step (c), a test substance that regulates the formation of the complex II is selected. The thus-selected test substance is useful as a regulator of the formation of elastic fibers or as a research reagent.

7.5. Screening Method for Substance Capable of Regulating the Formation of DANCE Complex Comprising at Least One DANCE and LTBP2 (Complex III) (Screening Method V)

The screening method V is not subject to limitation, as long as it enables an evaluation of the formation of the complex III, and it comprises, for example, the following steps (a), (b) and (c):

(a) contacting at least one DANCE with LTBP2 in the presence of a test substance;
(b) measuring the amount of the DANCE complex resulting from the step (a) above, and comparing the amount with the amount of the DANCE complex obtained in the absence of the test substance;
(c) selecting a test substance that regulates the formation of the DANCE complex on the basis of the results of the comparison in (b) above.

In the step (a), a test substance similar to that used in the screening method I can be used.

The contact of at least one DANCE and LTBP2 is the same as the contact mentioned in "6.3. DANCE complex comprising at least one DANCE and LTBP2 (complex III)".

In the step (b), the amount of the complex III can be measured by a combination of an immunoprecipitation method (see, for example, Example 6) and densitometry, an interaction analytical method such as surface plasmon resonance, a method based on ELISA, and the like.

A comparison of the amount of the complex III can be performed on the basis of the presence or absence of a significant difference in the amount of the complex III in the presence and absence of the test substance. Although the amount of the complex III in the absence of the test substance may be measured previously or simultaneously relative to the measurement of the amount of the complex III in the presence of the test substance, it is preferable to perform a simultaneous measurement, from the viewpoint of experimental accuracy and reproducibility.

Subsequently, in the step (c), a test substance that regulates the formation of the complex III is selected. The thus-selected test substance is useful as a regulator of the formation of elastic fibers or as a research reagent.

7.6. Screening Method for DANCE-Specific Protease (Screening Method VI)

The screening method VI comprises screening a DANCE-specific protease using an activity of cleaving DANCE as an index.

The DANCE-specific protease can be obtained from a cell expressing the protease. The cell expressing the DANCE-specific protease is similar to the cell mentioned in "2.2. Cleaving method".

For example, as the screening method VI, an expression cloning method can be used (see, e.g., Molecular Cloning, Second Edition; Current Protocols in Molecular Biology, Third Edition, Acad. Press (1993); Antibody Engineering: A Practical Approach, IRL Press at Oxford University Press (1996)).

Specifically, cDNA is prepared from the cell expressing a DANCE-specific protease and the cDNA is inserted into downstream of the promoter of an appropriate expression vector to prepare a recombinant expression vector, and thus a cDNA library is prepared. Transformants which express gene products derived from the cell expressing the DANCE-specific protease are obtained by introducing the recombinant expression vector into a host cell suitable for the expression vector, and a transformant which produces the DANCE-specific protease is selected therefrom. The, the DANCE-specific protease can be obtained by determining the gene sequence encoded by the cDNA introduced into the transformant which produces the DANCE-specific protease.

As the host cell used in the screening method VI, any cell which does not have an activity of cleaving DANCE, or whose activity of cleaving DANCE is extremely low, can be used. Whether or not certain cell has an activity of cleaving DANCE is evaluated by introducing the DANCE expression vector into the cell, and the confirming the expressed DANCE is cleaved or not.

As the cell used in the preparation of cDNA, the cell expressing the DANCE-specific protease, for example, cells such as fibroblast, 293T cell and arterial smooth muscle cell, and cells derived from tissue, such as lung tissue, uterine tissue and the like are used.

The preparation of cDNA libraly is carried out by the methods known per se. First, total RNA is prepared from a cell expressing the protease by an acidic thiocyanate guanidine-phenol-chloroform (AGPC) method or the like. Next, mRNA is prepared by the methods such as an oligo (dT) immobilized cellulose column method, or using a commercially-available kit (e.g., Quick Prep mRNA Purification Kit (manufactured by Pharmacia)). Subsequently, The cDNA library is produced from the prepared mRNA (e.g., Molecular Cloning, Second Edition, Current Protocols in Molecular Biology, Third Edition). The expression vector used for producing cDNA library is not particularly limited as long as it can express the insert in the used host cell.

The thus produced cDNA library may be used as such, however, a cDNA library produced by carrying out a subtraction method (Proc. Natl. Acad. Sci. USA, 85, 5783 (1988)) using mRNA of a cell which does not express DANCE-specific protease can also be used in order to concentrate the target gene.

In addition, when a cell which does not express DANCE is selected as a host cell, the DANCE expression vector is also introduced into the host cell, in addition to the cDNA library prepared as described above. As the introduction method of the recombinant vector into the host cell, any method can be used, so long as it is a method for introducing DNA into an animal cell. For example, electroporation method, calcium phosphate method and lipofection method can be mentioned.

A gene product encoded by the introduced cDNA can be expressed by culturing the transformant obtained as described above in a medium. Method for culturing the transformant in the medium can be carried out according to conventional methods used for culturing a host. For example, As the medium, RPMI1640 medium, αMEM medium, DMEM medium, 199 medium and medium supplementing these medium with fetal calf serum and the like, and the like can be used. The culturing is normally carried out under conditions such as pH 6-8, at 30-40° C. in the presence of 5% $CO_2$ for 1-7 days. Additionally, antibiotics such as kanamycin and penicillin may be optionally added through a period of culturing.

In the screening method VI, the transformant which produces a DANCE-specific protease can be selected by confirming the presence or absence or the degree of cleavage with western blotting or the like in the culture medium after culturing the aforementioned transformant. Optionally, a transformant in which the DANCE-specific expression vector is concentrated can be obtained by repeating the aforementioned steps plural times. Isolation of cDNA introduced into the selected transformant, and determination of gene sequence of the isolated cDNA can be carried out by the methods known per se.

The screening method VI can also be carried out by a method other than the expression cloning method. Specifically, the DANCE-specific protease can be purified by preparing an extract or culture supernatant of the cell expressing the DANCE-specific protease and fractionizing the extract or supernatant using an activity of cleaving DANCE as an index. The purification methods include, for example, solvent extraction method, salting out method with ammonium sulfate or the like, desalting method, precipitation method with an organic solvent, anion exchange chromatography method, cation exchange chromatography method, hydrophobic chromatography method, gel filtration method using a molecular sieve, affinity chromatography method, chromatofocusing method, and electrophoresis method such as isoelectronic focusing, and a combination of these methods.

Also, as the projects for analyzing human and other genomes have been completed, it is now also possible to screen for a DANCE-specific protease by cloning proteases on the basis of sequences registered with databases, information on expression sites and the like, and means such as homology search, and evaluating the DANCE cleavage activity of each of the proteases one by one. The finding has been obtained that a DANCE-specific protease is inhibited by aprotinin, which is a serine protease inhibitor. Therefore, in the present screening method, serine protease is preferentially screened for with a focus on efficiency.

This screening method VI is useful for enabling screening for a DANCE-specific protease. The DANCE-specific protease obtained by the screening method is useful as a regulator of the formation of elastic fibers (for example, for destroying elastic fibers), in the cleavage of DANCE, and for performing a screening method of the present invention.

8. Kit

The present invention also provides a kit comprising the following (a) and (b):
(a) DANCE or a polynucleotide having a nucleotide sequence that encodes DANCE;
(b) at least one component out of the following components (i) to (vi);

(i) DANCE which is a distinguishable form from the DANCE (a);
(ii) a polynucleotide having a nucleotide sequence that encodes a DANCE which is a distinguishable form from the DANCE (a);
(iii) lysyl oxidase;
(iv) a polynucleotide having a nucleotide sequence that encodes lysyl oxidase;
(v) LTBP2;
(vi) a polynucleotide having a nucleotide sequence that encodes LTBP2.

The kit of the present invention can also comprise an instruction manual bearing the statement that the kit should be, or can be, used to regulate the formation of elastic fibers, or to perform screening, and the like.

The kit of the present invention may comprise integrin, a polynucleotide having a nucleotide sequence that encodes integrin, lysyl oxidase-like-1, and a polynucleotide having a nucleotide sequence that encodes lysyl oxidase-like-1, in addition to the above-described components. These can be prepared by methods known per se.

The kit of the present invention may further comprise antibodies against DANCE, lysyl oxidase, LTBP2, integrin, and lysyl oxidase-like-1, in addition to the above-described components. These antibodies can be prepared in accordance with the above-described methods of preparing antibodies.

The kit of the present invention is useful for enabling the provision of a convenient means that enables other research concerning the above-described screening methods I to VI, and DANCE and the like, and as a regulator of the formation of elastic fibers (for example, for formation or maintenance of elastic fibers).

9. An Agent of Regulating the Formation of Elastic Fibers

The regulating agent of the present invention comprises a polypeptide of the present invention, an antibody, a DANCE mutant, a complex or a plurality of components constituting the complex, a DANCE-specific protease, a polynucleotide that encodes these, or the like.

The regulating agent of the present invention can be used as formulated with an optionally chosen carrier, for example, a pharmaceutically acceptable carrier, for preventing, treating, or improving a condition for which regulation of the formation of elastic fibers is desired.

For example, when the regulating agent of the present invention comprises an ingredient that forms or regenerates elastic fibers, the regulating agent is useful for preventing, treating, or improving a condition for which regulation of the formation of elastic fibers is desired, for example, pulmonary edema, blood vessel damage, cutis laxa, wounds, elastic fiber deterioration (for example, those caused by aging or ultraviolet), chapped skin, arteriosclerosis, and aortic aneurysm, or for cosmetic purposes.

When the regulating agent of the present invention comprises an ingredient that suppresses the formation of elastic fibers, the regulating agent is useful for preventing, treating, or improving a condition for which suppression of the formation of elastic fibers is desired, for example, myocardial infarction.

The pharmaceutically acceptable carrier is exemplified by, but not limited to, excipients such as sucrose, starch, mannit, sorbit, lactose, glucose, cellulose, talc, calcium phosphate, calcium carbonate and the like, binders such as cellulose, methylcellulose, hydroxypropylcellulose, polypropylpyrrolidone, gelatine, gum arabic, polyethylene glycol, sucrose, starch and the like, disintegrating agents such as carboxymethyl cellulose, hydroxypropyl starch, sodium-glycol-starch, sodium hydrogen carbonate, calcium phosphate, calcium citrate and the like, lubricants such as magnesium stearate, aerosil, talc, sodium lauryl sulfate and the like, aromatics such as citric acid, menthol, glycyl lysine ammonium salt, glycine, orange powder and the like, preservatives such as sodium benzoate, sodium bisulfite, methylparaben, propylparaben and the like, stabilizers such as citric acid, sodium citrate, acetic acid and the like, suspending agents such as methylcellulose, polyvinylpyrrolidone, aluminum stearate and the like, dispersing agents such as surfactant and the like, diluents such as water, physiological saline, orange juice and the like, base wax such as cacao butter, polyethylene glycol, refined kerosene and the like, and the like.

A preparation which is suitable for oral administration is, for example, a liquid comprising an effective amount of a ligand dissolved in a diluent such as water, physiological saline and orange juice, a capsule, sachet or tablet comprising an effective amount of a ligand as a solid or granules, a suspension comprising an effective amount of a ligand in a suitable dispersion medium, an emulsion comprising a solution of an effective amount of a ligand dispersed and emulsified in a suitable dispersion medium and the like.

A preparation preferable for parenteral administration (e.g., subcutaneous injection, intramuscular injection, topical injection, intraperitoneal administration and the like) includes, for example, an aqueous or non-aqueous isotonic sterile injection which may contain antioxidant, buffer, bacteriostatic agent, isotonicity agent and the like. It may be an aqueous or non-aqueous sterile suspension which may contain suspension, solubilizer, thickener, stabilizer, preservative and the like. The preparation can be sealed in a container in a unit dose or plural doses like an ampoule or vial. It is also possible to lyophilize a ingredient and a pharmaceutically acceptable carrier and preserve them in a state that only requires dissolving or suspending in a suitable sterile vehicle immediately before use.

While the dose of the preparation of the present invention varies depending on the kind and activity of the ingredient, degree of seriousness of the disease, the animal species to be the administration subject, drug acceptability, body weight and age of the administration subject, and the like, it is generally about 0.0008-about 2.5 mg/kg a day for an adult in the amount of the ingredient.

The contents of all the references cited herein are hereby incorporated in their entireties by reference, to the extent that they have been disclosed herein.

The present invention is explained in more detail by referring to Examples, which are mere illustration and not to be construed as limitative.

EXAMPLES

1. Materials and Methods 1.1. Construction of Expression Plasmids

The expression plasmids used in the present invention were prepared as described below. All these constructs were used in the expression experiments after the nucleotide sequences thereof were confirmed.

pEF6/ssFLAG:

The synthetic nucleotide ggtaccgctagcgaattcaccatgtctgcacttctgatcctagctcttgttggagctgcagt tgctgactacaaagacgatgacgacaagactagtcatcatcaccatcaccattctagagaag gatccgatatccgcgccgcatcgattgactagctgaggccgcaaaccc (SEQ ID NO:17) and a synthetic nucleotide with a strand complementary thereto were inserted into the Kpn I-Pme I site of pEF6/V5-A plasmid (Invitrogen). Thereby Kpn I-Nhe I-EcoRI-prepro trypsin signal peptide (MSALLILALVGAAVA (SEQ ID NO:18))-FLAG tag (DYKDDDDK (SEQ ID NO:19))-Spe I-6×His tag (HHHHHH (SEQ ID NO:20))-Xba I-BamHI-EcoRV-Not 1-Cla I is located downstream of the elongation factor promoter and upstream of the bovine growth hormone polyadenylation sequence.

pEF6/ssMyc:

The synthetic nucleotide gaattcaccatgtctgcacttctgatc-ctagctcttgttggagctgcagttgctgactacga agaggacgaacaaaaact-catctcagaagaggatctgactagt (SEQ ID NO:21) and a synthetic nucleotide with a strand complementary thereto were inserted into the EcoRI-Spe I site of pEF6/ssFLAG plasmid. Thereby Kpn I-Nhe I-EcoRI-prepro trypsin signal peptide (MSALLILALVGAAVA (SEQ ID NO:18))-Myc tag (EQKLISEEDL (SEQ ID NO:22))-Spe I-6×His tag (HHHHHH (SEQ ID NO:20))-Xba I-BamHI-EcoRV-Not 1-Cla I is located downstream of the elongation factor promoter and upstream of the bovine growth hormone polyadenylation sequence.

pEF6/FLAG:

The synthetic nucleotide tggtaccgagctcggatccactagtc-cagtgtggtggaattctgcagatatccagcacagtg gcggccgtctagagacta-caaagacgatgacgacaagagagggtctcatcatcaccatcacc attgagcggc-cgcaaaccc (SEQ ID NO:23) and a synthetic nucleotide with a strand complementary thereto were inserted into the Kpn I-Pme I site of the pEF6/V5-A plasmid (Invitrogen). Thereby Kpn I-BamHI-Spe I-EcoRI-EcoRV-Xba I-FLAG tag (DYKDDDDK (SEQ ID NO:19))-6×His tag (HHHHHH (SEQ ID NO:20))-stop codon-Not I is located downstream of the elongation factor promoter and upstream of the bovine growth hormone polyadenylation sequence.

pEF6/ssFLAG-hDANCE:

The portion from the 25th amino acid to the stop codon of a human DANCE consisting of the amino acid sequence shown by SEQ ID NO:2 was amplified by a PCR method using the primers tctagagcacagtgcacgaatggctttg (SEQ ID NO:24) and gcggccggtcagaatgggtactgcgacacatatccg (SEQ ID NO:25) and cloned into pCR4-Blunt Topo (Invitrogen) by the method described in the instructions for the product; after the sequence was confirmed, cleavage with Xba I-Not I was performed, and the fragment obtained was inserted into the Spe I-Not I site of pEF6/ssFLAG.

pEF6/ssMyc-hLTBP2:

The portion from the 36th amino acid to the stop codon of human LTBP2 was amplified by a PCR method using tctaga-caaagggaccccgtagggagatacgag (SEQ ID NO:26) and gcggc-cgcctggtactccttggcagtgcagtggg (SEQ ID NO:27), and the amplified fragment was inserted into the Spe I-Not I site of pEF6/ssMyc in the same manner as described above.

pEF6/hDANCE-FLAG:

The portion from the 1st amino acid to the last 448th amino acid of a human DANCE consisting of the amino acid sequence shown by SEQ ID NO:2 was amplified by a PCR method using the primers gaattcttcttctcgccttcgcatctcctcc (SEQ ID NO:28) and tctagagaatgggtactgcgacacatatccg (SEQ ID NO:29); after cloning and sequencing were performed in the same manner as described above, cleavage with EcoRI-Xba I was performed, and the fragment obtained was inserted into the EcoRI-Xba I site of pEF6/FLAG (FIG. 1).

pEF6-hDANCE(R77A)-FLAG:

The 77th amino acid of human DANCE, arginine, was substituted with alanine using the Quick Change in vitro mutagenesis kit (Stratagene). The other procedures were the same as pEF6-hDANCE-FLAG.

pEF6-hDANCE ΔND-FLAG:

Each of the portions from the 1st amino acid to the 26th amino acid and from the 78th amino acid to the 448th amino acid of human DANCE consisting of the amino acid sequence shown by SEQ ID NO:2 was amplified by a PCR method, and the amplified fragments were ligated at the Nhe I site, after which the ligation product was inserted into the EcoRI-Xba I site of pEF6/FLAG (FIG. 1).

pEF6-hDANCE ΔN-FLAG:

Each of the portions from the 1st amino acid to the 26th amino acid and from the 113th amino acid to the 448th amino acid of human DANCE consisting of the amino acid sequence shown by SEQ ID NO:2 was amplified by a PCR method, and the amplified fragments were ligated at the Nhe I site, after which the ligation product was inserted into the EcoRI-Xba I site of pEF6/FLAG (FIG. 1).

pEF6-hDANCE ΔM-FLAG:

Each of the portions from the 1st amino acid to the 112th amino acid and from the 315th amino acid to the 448th amino acid of human DANCE consisting of the amino acid sequence shown by SEQ ID NO:2 was amplified by a PCR method, and the amplified fragments were ligated at Nhe I site, after which the ligation product was inserted into the EcoRI-Xba I site of pEF6/FLAG (FIG. 1).

pEF6-hDANCE ΔC-FLAG:

The portion from the 1st amino acid to the 315th amino acid of human DANCE consisting of the amino acid sequence shown by SEQ ID NO:2 was amplified by a PCR method, and the amplified fragment was inserted into the EcoRI-Xba I site of pEF6/FLAG (FIG. 1).

The 22nd amino acid to the 417th amino acid of the polypeptide (417 amino acids) encoded by human lysyl oxidase (GenBank accession number: AF039291.1) cDNA was amplified by a PCR method and incorporated in the XbaI/NotI site of pEF6/ssMyc.

1.2. Cells and Transfection 293T cells were used in expression experiments. Transfection was performed using the Lipofect AMINE Plus reagent as directed in the product instructions. 24 hours after transfection, the medium was exchanged with serum-free medium, and cultivation was continued for 48 hours; the resulting supernatant or cell lysate was used for Western blotting and in vitro binding assay.

Neonatal mouse skin fibroblasts were collected and cultured by the methods described in "Current Protocols in Cell Biology".

Bovine arterial smooth muscle was purchased from Cambrex.

1.3. Recombinant DANCE

A cell line showing stable expression of human DANCE was prepared using 293T cells and pEF6-hDANCE-FLAG, and the recombinant DANCE was purified from the culture supernatant using Ni-NTA agarose (Qiagen), after which the purified solution was desalinized using a desalinization column (Amersham).

1.4. Antibodies

The anti-mouse DANCE antibody BSYN1923 was prepared by immunizing a rabbit with a synthetic peptide corresponding to the mouse DANCE 76-98 amino acid, and affinity-purified using a column with an antigen peptide immobilized thereon. Anti-elastin monoclonal antibody was purchased from Chemicon and Elastin Products Company (EPC); fibrillin 1 polyclonal antibody and monoclonal antibody, fibrillin 2 polyclonal antibody, and LTBP2 monoclonal antibody were purchased from EPC. Anti-FLAG M2 antibody and anti-FLAG M2 agarose were purchased from Sigma; anti-Myc (9E10) antibody was purchased from Santa Cruz. Polyclonal anti-elastin antibody (PR533) was purchased from Elastin Products Company, INC. Anti-rabbit Alexa Fluor 488 antibody and anti-mouse Alexa Fluor 546 antibody were purchased from Molecular Probes.

1.5. Metabolabelling with 35S-Met and Cys, Immunoprecipitatation, In Vitro Binding Assay, and Western Blotting These were performed by methods described in "Molecular Cloning, 3rd Ed.".

1.6. Cultivation of Fibroblasts

Human fibroblasts were kindly supplied by the Department of Plastic Surgery, Kyoto University Hospital. A cover glass was placed on the bottom of a 24-well plate, on which human fibroblasts were seeded at $7.5 \times 10^4$ cells per well, and cultured in a DMEM medium supplemented with 10% FBS at 37° C. in the presence of 5% $CO_2$. After the plate washed with PBS on Day 3, the medium was exchanged with a DMEM/F12 medium not supplemented with FBS, and purified DANCE protein, cleaved form of DANCE protein 4 μg/ml, or FBS was added. Cultivation was continued at 37° C. in the presence of 5% $CO_2$, and the cells were fixed and immunologically stained on Day 14.

1.7. Immunostaining

On Day 14 of cultivation, the cells were washed with 1 ml of PBS three times, after which they were fixed with 100% methanol at −20° C. for 30 minutes. After washing with PBS, the cells were subjected to blocking with a PBS containing 2% BSA at room temperature for 30 minutes, after which the cells were incubated with the polyclonal anti-elastin antibody (dilution rate 1/100) and the monoclonal anti-FLAG antibody (dilution rate 1/100) at room temperature for at least 1 hour. The cells were washed with PBS and further incubated with the anti-rabbit Alexa Fluor 488 antibody (dilution rate 1/100) and the anti-mouse Alexa Fluor 546 antibody (dilution rate 1/100) at room temperature for 1 hour. After washing with PBS, the cells were fixed with 4% para-formaldehyde at room temperature for 10 minutes and again washed with PBS, after which the sample was mounted onto a glass slide using a DAPI-containing Vectashield. Examination was performed using a confocal microscope.

Example 1

Some DANCE has been Cleaved at N-Terminus In Vitro and In Vivo 1.1. Forced Expression of Human and Mouse DANCE in 293T Cells Human and mouse DANCE cDNAs with FLAG tag added immediately downstream of the signal peptide cleavage site were transfected to 293T cells; after the medium was exchanged with serum-free medium, cultivation was continued for 48 hours, 15 μl of the culture supernatant was developed by SDS-PAGE, and Western blotting was performed. The antibodies used were BSYN obtained by immunizing a rabbit with a peptide corresponding to mouse the DANCE 76-98th amino acids, and anti-FLAG M2 antibody.

Figure 2:
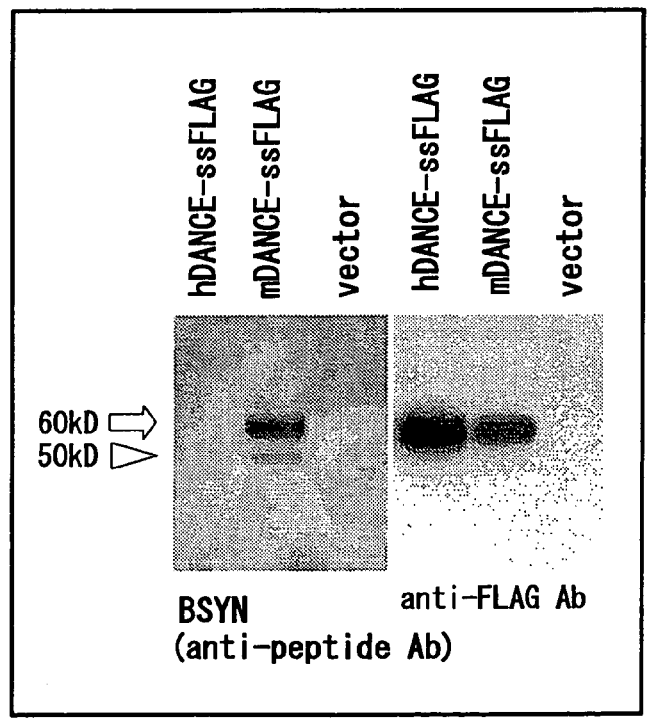
FIG. 2 shows the forced expression of human and mouse DANCEs in 293T cells.

As a result, as shown in FIG. 2, BSYN did not recognize human DANCE, and mouse DANCE was detected as two bands. In contrast, anti-FLAG M2 antibody detected human and mouse DANCE as a single band.

1.2. Expression of DANCE in Mouse-Derived Skin Fibroblasts

Fibroblasts from skins of neonatal DANCE knockout mice [see Nature 415: 171-175 (2002)] and control mice of the same litter were cultured and labeled with $^{35}$S-Met and Cys for 24 hours, after which the culture supernatant was immunoprecipitated with BSYN antibody. The immunoprecipitate was developed by SDS-PAGE and detected by autoradiography.

Figure 3:
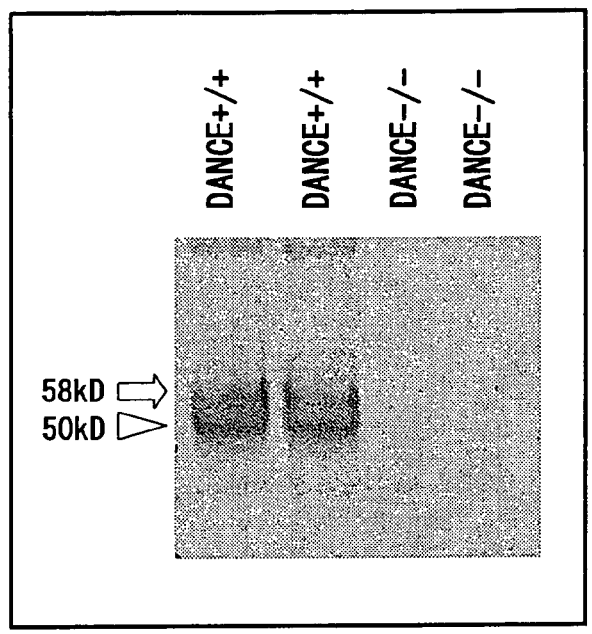
FIG. 3 shows the expression of DANCE in culture supernatants of mouse skin fibroblasts.

As a result, two bands were detected in the skin fibroblasts from the DANCE+/+ mice, whereas no bands were detected in the skin fibroblasts from the DANCE−/− mice (FIG. 3).

1.3. Western Blot of Mouse Lung Tissue

Lung tissue extracts from 12-week-old DANCE knockout mice and control mice of the same litter were developed by SDS-PAGE and Western blotting was performed with BSYN antibody.

Figure 4:
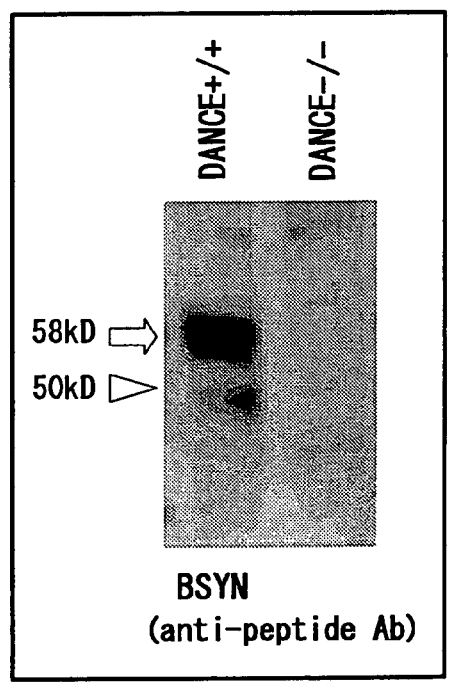
FIG. 4 shows Western blotting of mouse lung tissue.

As a result, DANCE was detected as two bands in the lung tissue of the DANCE+/+ mice, whereas no bands were detected in the lung tissue of the DANCE−/− mice (FIG. 4).

Example 2

Figure 5:
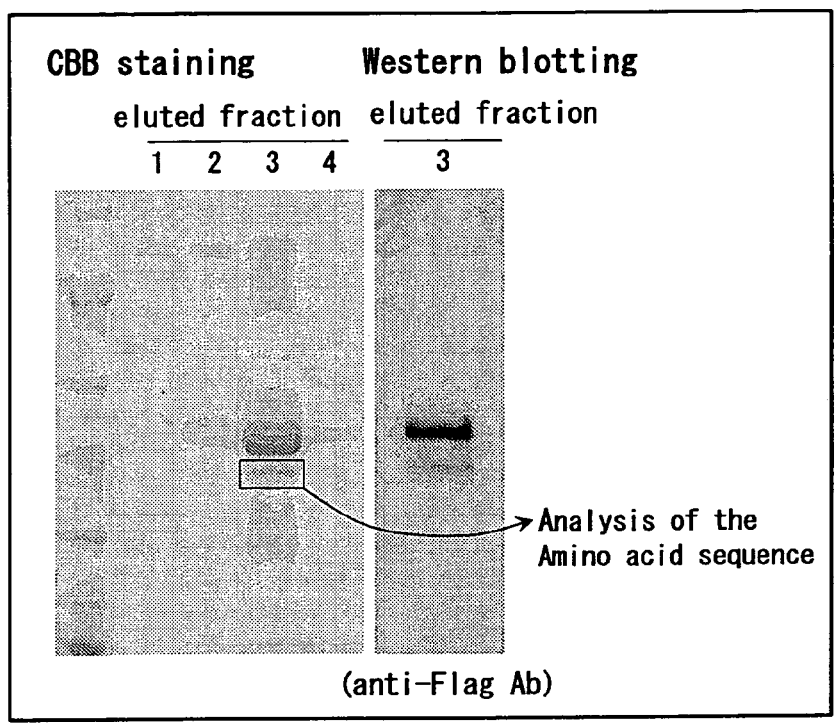
FIG. 5 shows the purification of full-length DANCE and N-terminal-cleaved form of DANCE.

N-terminus of Cleaved Form of DANCE Agrees with the 78th and Following Amino Acids of DANCE A human DANCE cDNA with FLAG tag and 6×His tag added to the carboxyl terminus thereof was transfected to 293T cells to establish a cell line showing stable expression. The recombinant DANCE was purified from 800 ml of the serum-free culture supernatant using Ni-NTA agarose (Qiagen), developed by SDS-PAGE, and stained with Coomassie-Blue. Of the major two bands, the band corresponding to the cleaved form of DANCE was cut out and analyzed by Edman degradation to determine the N-terminal amino acid sequence thereof (FIG. 5).

As a result, the N-terminal amino acid sequence of the cleaved form of DANCE agreed with the amino acid sequence at the 78th and subsequent positions of DANCE.

Hence, it was considered that this low-molecular protein is produced due to the cleavage of DANCE between the 77th amino acid and the 78th amino acid.

Example 3

Cleavage of DANCE is Inhibited by Serine Protease Inhibitor

A human DANCE cDNA with FLAG tag and 6×His tag added to the carboxyl terminus thereof was transfected to 293T cells; the cells were cultured using a serum-free medium comprising a cysteine protease inhibitor (E64) or serine protease inhibitor (aprotinin) for 48 hours; a recombinant protein was precipitated from the culture supernatant using Ni-NTA agarose and was developed by SDS-PAGE and Western blotting was performed using anti-FLAG M2 antibody.

Figure 6:
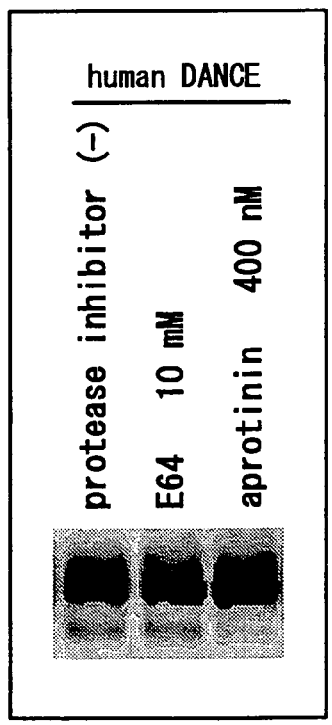
FIG. 6 shows the inhibition of DANCE cleavage with a serine protease inhibitor.

As a result, the cleavage of DANCE was not inhibited by E64 but inhibited by aprotinin (FIG. 6).

Hence, it was suggested that DANCE is cleaved by serine protease.

Example 4

DANCE Becomes Unlikely to be Cleaved if Arg77 is Substituted with Ala

Figure 7:
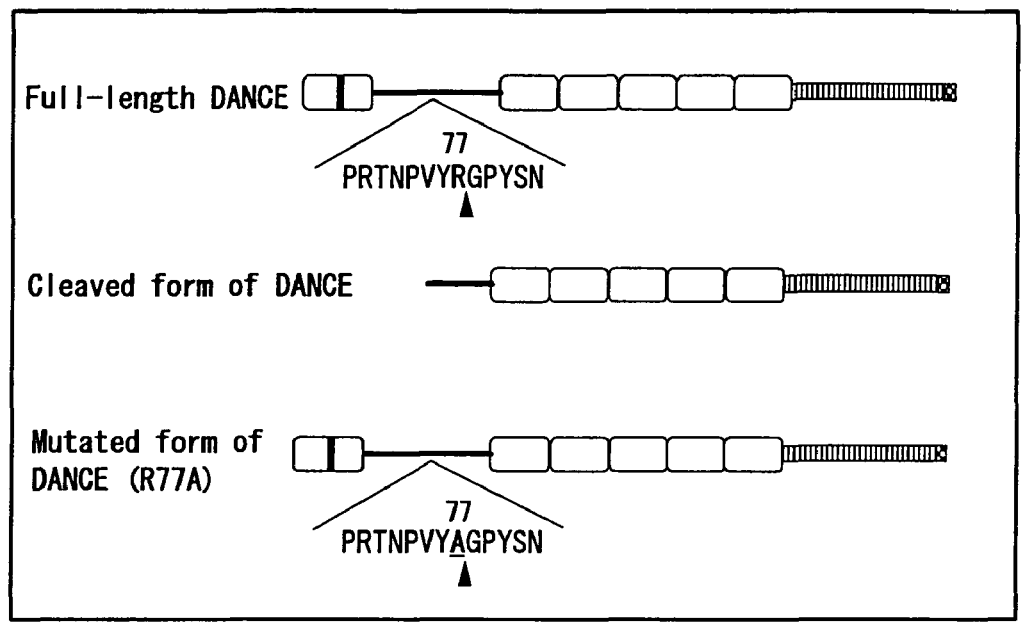
FIG. 7 shows the human DANCE cleavage site in an in vitro culture, and the amino acid mutation site of a mutated form of DANCE.

An expression vector for the mutated form of DANCE resulting from the substitution of the 77th arginine of DANCE with alanine (with C-terminal FLAG and 6×His tag) (FIG. 7), and an expression vector for normal form of DANCE (with C-terminal FLAG and 6×His tag) were transfected to 293T cells; the cells were cultured using serum-free medium for 48 hours; a recombinant protein was precipitated from the culture supernatant using Ni-NTA agarose, and developed by SDS-PAGE, and Western blotting was performed using anti-FLAG M2 antibody.

Figure 8:
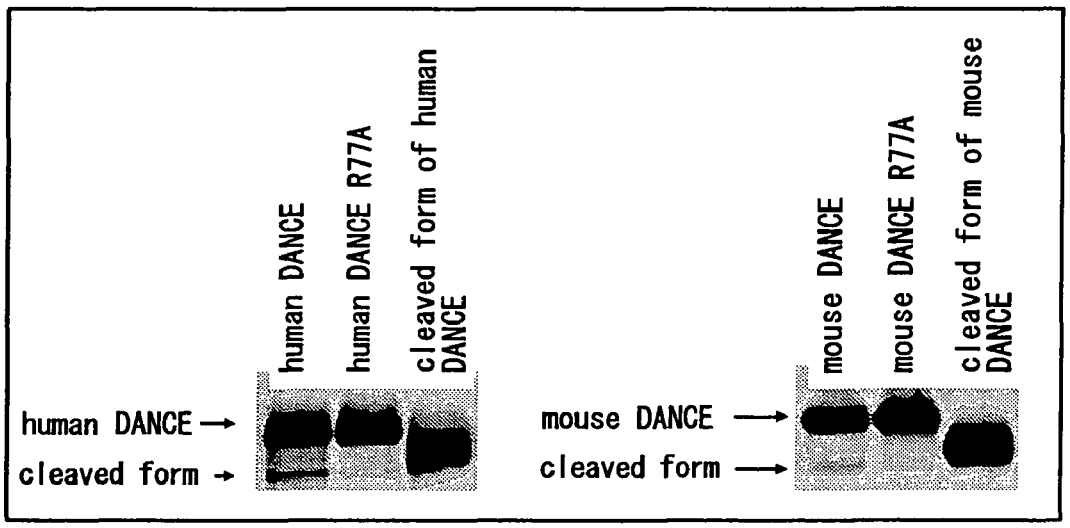
FIG. 8 shows reductions in the amount of DANCE cleaved in a mutated form of DANCE (R77A).

As a result, this mutated form of DANCE was shown to exhibit resistance to cleavage with a protease (FIG. 8).

Example 5

DANCE Forms a Homo-Complex and Also Binds to LTBP2

After bovine arterial smooth muscle cells seeded on a 9-cm plate were labeled with 35S-Met and Cys for 24 hours, the culture supernatant and 50 μg of recombinant human DANCE (with C-terminal FLAG and 6×His) were mixed and precipitated with anti-FLAG agarose (Sigma), and the resulting precipitate was developed by SDS-PAGE and autoradiography was performed. The same culture supernatant was immunoprecipitated with commercially available antibodies against elastic fiber constituent protein (elastin, fibrillin 1, fibrillin 2 and LTBP2), and developed with the same SDS-PAGE gel, and autoradiography was performed.

Figure 9:
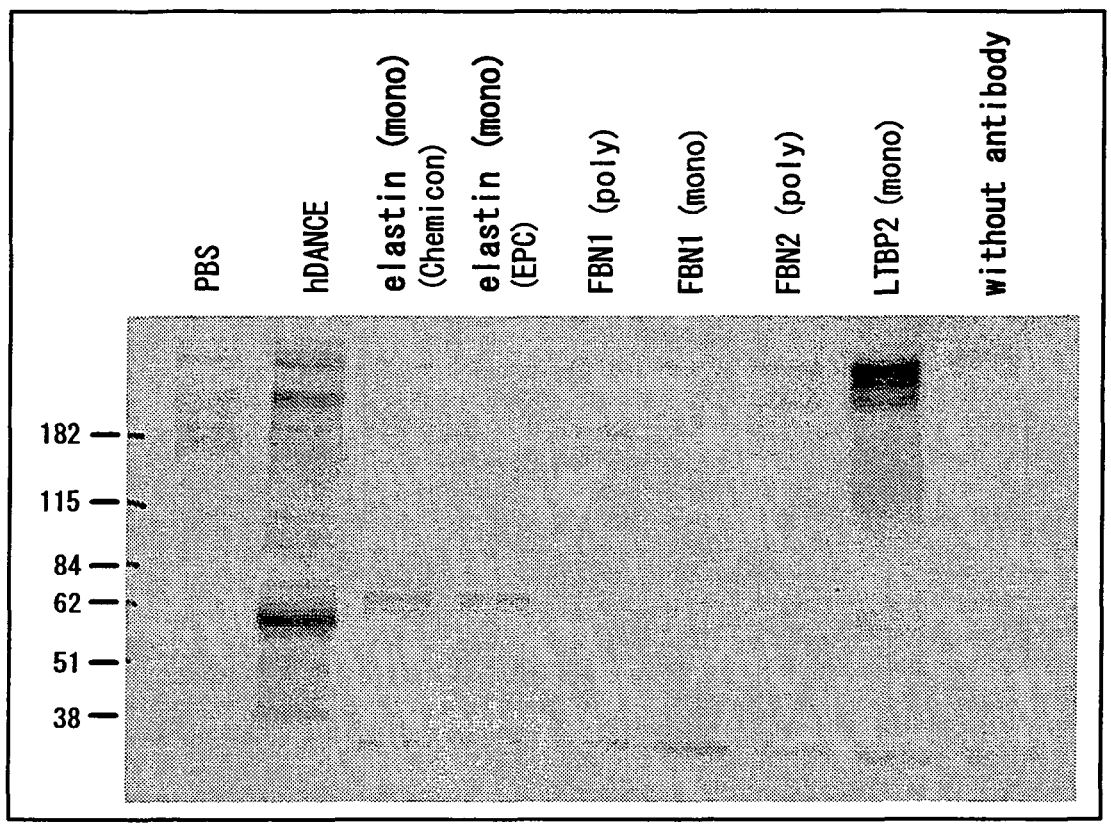
FIG. 9 shows DANCE-binding proteins in a culture of smooth muscle cells.

As a result, it was shown that DANCE forms a homo-complex, and that DANCE binds to LTBP2 (FIG. 9).

Example 6

Analysis of Binding Region for Human DANCE and DANCE or LTBP2

From the results of Example 5, the binding region of DANCE to each other and the binding region of DANCE to LTBP2 were analyzed.

A human DANCE construct with FLAG tag (FIG. 8), a human DANCE construct with Myc tag, and a human LTBP2 construct were separately transfected to 293T cells. After cultivation in serum-free medium for 48 hours, each culture supernatant and cell extract were mixed, and this was used as the protein solution. A protein solution from the DANCE construct with FLAG tag and a protein solution from DANCE or LTBP2 with Myc tag were mixed on ice for 1 hour, and precipitated with anti-FLAG antibody, and the resulting precipitate was developed by SDS-PAGE, and detected using anti-Myc antibody or anti-FLAG antibody.

Figure 10:
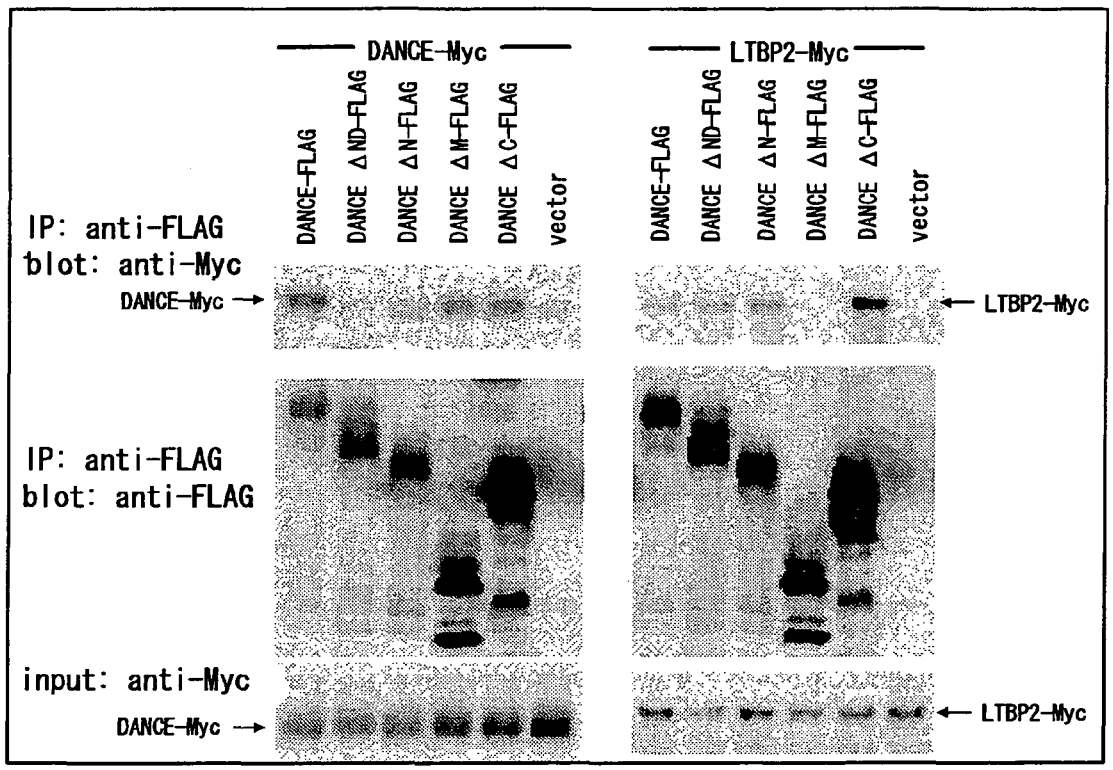
FIG. 10 shows analyses of regions necessary for the binding between DANCEs and binding of DANCE and LTBP2 using DANCE-deleted mutants.

As a result, it was found that the binding of DANCE to each other requires the N-terminal domain, and the binding of DANCE to LTBP2 requires the central domain of DANCE (FIG. 10). It was also found that the binding of DANCE and LTBP2 is stronger when the N-terminal or C-terminal domain of DANCE is lacked.

Example 7

DANCE is Capable of Binding to Lysyl Oxidase

The present inventors found that the phenotype of lysyl oxidase gene-deficient mice [J. Biol. Chem. 278(16): 14387-93 (2003); Circulation 106(19): 2503-9 (2002)] is closely similar to the phenotype of DANCE gene-deficient mice previously reported by the inventors [Nature 415: 171-175 (2002)]. Hence, the present inventors considered that the formation of a complex between DANCE and lysyl oxidase may be important for DANCE to exhibit the function thereof, and determined whether or not DANCE binds to lysyl oxidase. The assay was performed in the same manner as Example 6 except that a precipitate obtained using anti-FLAG antibody was developed by SDS-PAGE and detected using anti-Myc antibody.

Figure 11:
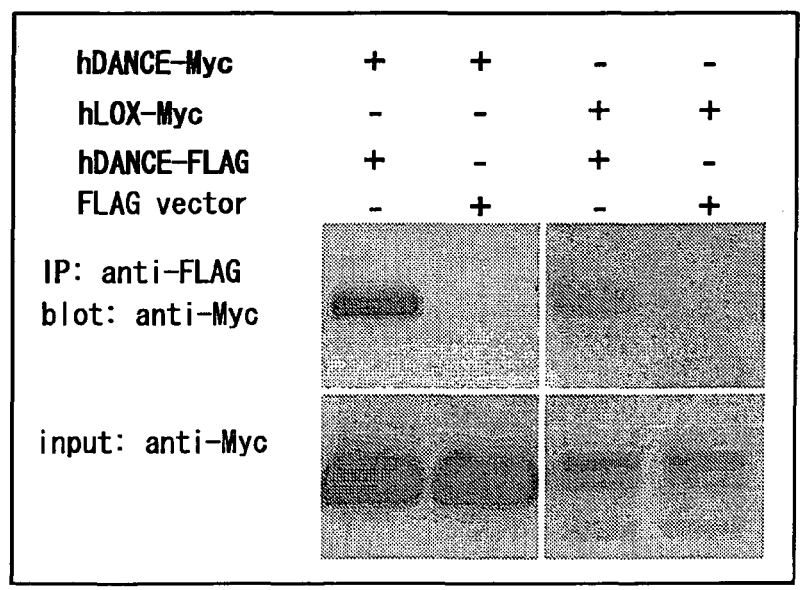
FIG. 11 shows the binding of DANCE and lysyl oxidase.

As a result, DANCE was suggested to bind to lysyl oxidase (FIG. 11).

Discussion

1. Binding of DANCE and LTBP2

The present inventors found that DANCE specifically binds to LTBP2. This binding occurs via the domain at the center of DANCE wherein a calcium-binding EGF-like motif is present in a series. To date, the present inventors have reported that the amino-terminal domain of DANCE binds to cell surface integrin, and Liu et al. have reported that DANCE binds to LOXL1 in half the carboxyl-terminal side thereof. However, elastin is known to deposit along microfibril, rather than deposit in close contact with the cell surface, and to become mature elastic fibers [Matrix Biol. 19: 455-6 (2000)]. Therefore, if the binding of DANCE and LOXL1 promotes the deposition and crosslinking of elastin to microfibril, DANCE should have bound to microfibril. Microfibril is a long extracellular fiber, and is considered to compose of oblong protein molecules such as fibrillin 1, fibrillin 2, and LTBP2. Fibrillin knockout mice, whether the fibrillin is fibrillin 1 or fibrillin 2, do not suffer elastic fiber dysplasia, and the binding of fibrillin and DANCE is unlikely. Although LTBP2 is a protein that does not bind to latent TGFβ despite that it belongs to the LTBP family, and that is localized in elastic fibers, the role thereof in a living organism remains unclear because LTBP2 knockout mice are fatal in early fetal period [Mol. Cell Biol. 20: 4879-87 (2000)]. The present finding by the present inventors suggests that LTBP2 localize elastin-crosslinking enzyme in microfibril by anchoring DANCE onto microfibril, thus helping the deposition and crosslinking of elastin along microfibril.

2. Binding of DANCE to Each Other

Although it remained unclear whether DANCE works in the form of a monomer, dimer or multimer, DANCE was identified as the major DANCE-binding protein present in smooth muscle culture supernatant in this study. This indicates that DANCE forms a homo-complex (dimer or multimer). The binding of DANCE to each other is mediated by the amino-terminal domain thereof. Previously, the present inventors showed that the amino-terminal domain of DANCE binds to cell surface integrin [J. Biol. Chem. 274(32): 22476-22483 (1999)], and the present data implies that the binding of DANCE to each other is promoted as a new function of the amino-terminal domain thereof.

3. Cleavage of Amino-Terminal Domain of DANCE

The present inventors found that some DANCEs are cleaved at the amino-terminal domain thereof in vivo and in vitro. This cleavage is caused by an unidentified serine protease; if the arginine at the cleavage site is substituted with alanine, the cleavage becomes unlikely. As postulated from the function of the amino-terminal domain of DANCE, cleaved form of DANCE (1) no longer binds to cell surface integrin, (2) the DANCE no longer binds to each other, and (3) a cleaved form of DANCE exhibits stronger binding with LTBP2 than full-length DANCE. These new findings (1) to (3) suggest that in a living organism the cleavage of DANCE with a protease serves as a mechanism for controlling the functional changes of DANCE, and hence the formation of elastic fibers. Based on this idea, drug-induced inhibition or promotion of DANCE cleavage protease can be useful in preventing the deterioration of elastic fibers and promoting the regeneration thereof.

4. Binding of DANCE and Lysyl Oxidase

LOX1 gene-deficient mice exhibit abnormalities in the formation of elastic fibers. LOXL1 is considered to associate directly with DANCE and anchored by DANCE to the site of the formation of elastic fibers to crosslink elastin. However, the phenotype of LOXL1 gene-deficient mice is weaker than the phenotype of DANCE gene-deficient mice; the entire action of DANCE cannot be explained solely by binding with LOXL1. Although lysyl oxidase gene-deficient mice also exhibit abnormalities in the formation of elastic fibers, the binding of DANCE and lysyl oxidase, which the present inventor found at the present occasion, suggests that DANCE makes the crosslinking of elastin to occur efficiently by anchoring lysyl oxidase.

Example 8

Screening for Substance that Regulates the Cleavage of DANCE

A human DANCE cDNA with FLAG tag and 6×His tag added to the carboxyl terminus thereof is transfected to 293T cells, the cells are cultured using serum-free medium in the presence and absence of a test substance for 48 hours; human DANCE is precipitated from the culture supernatant using Ni-NTA agarose and developed by SDS-PAGE, and Western blotting is performed using anti-FLAG M2 antibody. By quantitatively analyzing the two bands in the presence and absence of the test substance, whether or not the test substance is capable of regulating the cleavage of DANCE is determined.

Example 9

Figure 12:
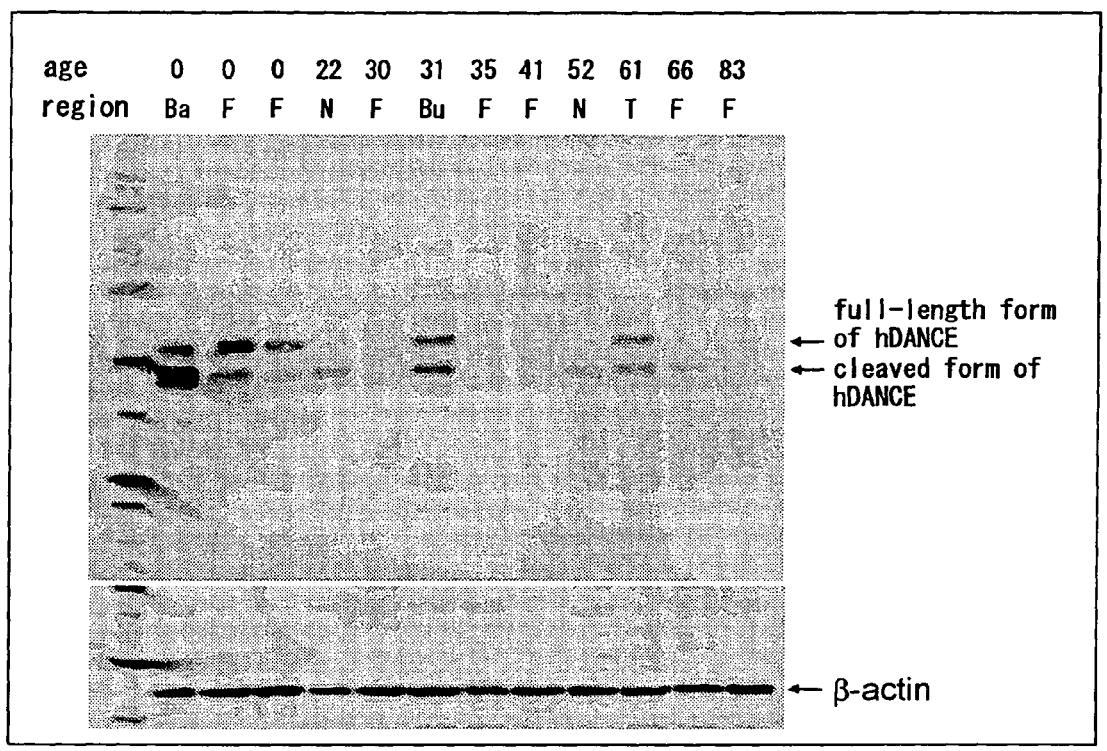
FIG. 12 shows the expression of DANCE protein in skins of humans at various ages. Extra skins (with inflammation) obtained at tumor extirpation from various tissues: Ba: back; F: face; N: neck; Bu: buttock; T: lip

Expression of Full-Length and Cleaved Form of DANCE in the Skins of Humans at Various Ages To examine the expression of DANCE in skin tissue extirpated during a plastic surgery operation, Western blotting was performed using anti-human DANCE antibody (FIG. 12). Although the full-length and cleaved form of DANCE protein were detectable from all samples, major differences in the expression level were observed depending on age and skin collection site. First, in the facial skin, both the full-length DANCE and cleaved form of DANCE were expressed at high levels, with particularly higher expression of the full-length DANCE in 0-year-old babies, whereas in adults, there was the tendency for lower expression of both the full-length DANCE and cleaved form of DANCE, with particularly lower expression of full-length DANCE. In the skins at other sites not exposed to light, there was the tendency for reasonable levels of expression maintained for both full-length DANCE and cleaved form of DANCE even in adults.

Reference Example 1

Cleaved Form of DANCE has No Integrin-Mediated Cell Adhesion Promoting Activity

Figure 13:
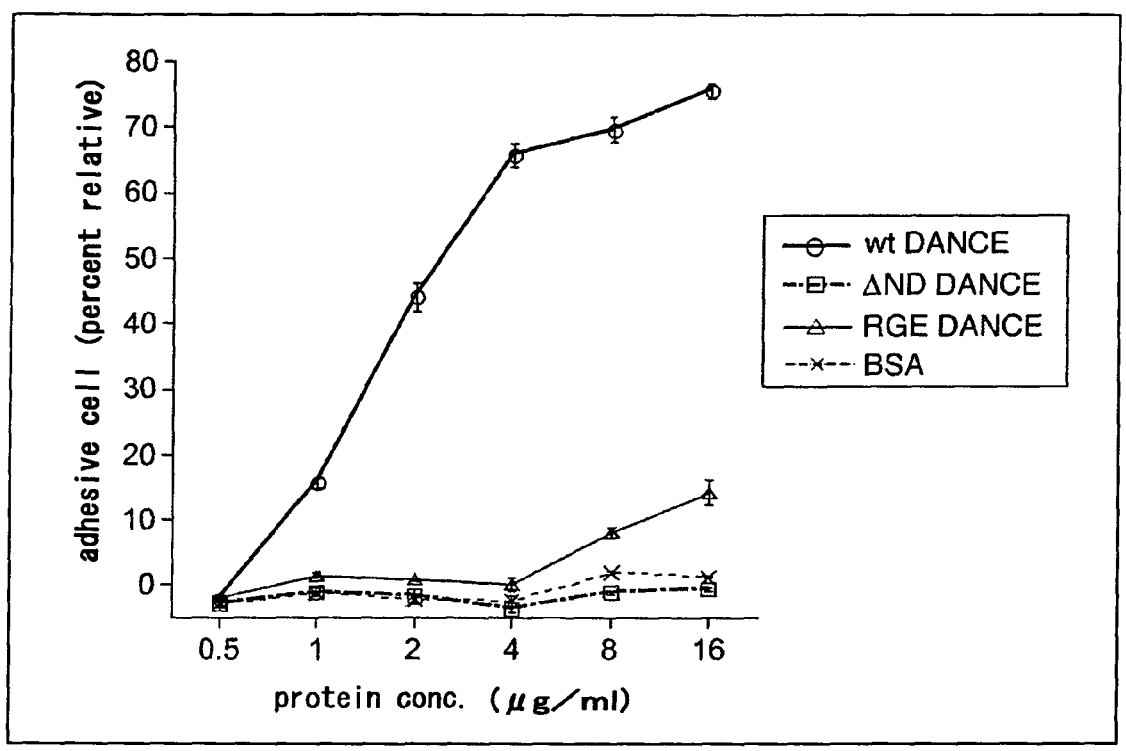
FIG. 13 shows the results of a cell adhesion assay of mutant DANCE proteins to vascular endothelial cells.

Full-length DANCE promotes the adhesion and extension of vascular endothelial cells via cell surface integrin. The present inventor has reported to date that full-length DANCE can serve as a ligand for the integrins αvβ3, αvβ5, and α9β1. Since the domain serving as the ligand is considered to be around the RGD motif of the amino-terminal domain of DANCE, each recombinant protein of a DANCE mutant wherein RGD was replaced with RGE for one-amino-acid substitution (RGE DANCE), and amino-terminal cleaved form of DANCE (ΔND DANCE) were purified, and these, along with full-length DANCE, were subjected to vascular endothelial cell adhesion assay (FIG. 13). In the case of full-length DANCE, cell adhesion was promoted with dependence on the concentration of the protein used for coating, whereas RGE DANCE had almost no cell adhesion activity and ΔND DANCE had absolutely no cell adhesion activity.

Reference Example 2

The Amino-Terminal Domain of DANCE is Necessary for the Formation of Elastic Fibers Subsequently, whether or not the cleavage of the amino-terminal domain of DANCE with a protease influences the formation of elastic fibers was examined.

Human skin fibroblasts were seeded to reach confluency; the medium was replaced with serum-free medium or a medium containing 10% fetal calf serum; the cells were cultured for 2 weeks; the formation of elastic fibers was analyzed by immunostaining with anti-elastin antibody.

As a result, with the medium containing 10% fetal calf serum, formation of elastic fibers was observed. Although cells survived in the serum-free medium, elastic fibers were hardly formed. However, when recombinant DANCE had been added to serum-free medium at 4 μg/ml, elastic fibers were formed at a higher level than with the serum-containing medium. When the localization of the recombinant DANCE added at that time was examined using anti-FLAG antibody, it was found to be co-localized with the elastic fibers formed. On the other hand, with the medium supplemented with ΔND-DANCE, the formation of elastic fibers was very little; it was considered that ΔND-DANCE has almost no activity to form elastic fibers, or a very weak activity.

Hence, because the cleavage of the amino-terminal domain of DANCE with a protease is considered to represent DANCE inactivation, an inhibitor of DANCE cleavage protease is expected to serve usefully as a drug for forming or maintaining elastic fibers by increasing full-length DANCE.

INDUSTRIAL APPLICABILITY

A screening method of the present invention enables the development of a pharmaceutical of a new mechanism of action allowing the regulation of the formation of elastic fibers, or the identification of a DANCE-specific protease. The measurement method of the present invention enables a diagnosis of the status of the formation of elastic fibers. Furthermore, the polypeptide, antibody, complex and kit of the present invention are preferable for performing a method of the present invention, preventing, treating, or improving a condition for which regulation of the formation of elastic fibers is desired, or as a research/diagnostic reagent and the like.

The present application is based on a patent application No. 2004-096685 filed in Japan on Mar. 29, 2004, and its content is herein incorporated by reference.

The invention claimed is:

1. An isolated polypeptide consisting of the amino acid sequence shown by SEQ ID NO:6; the amino acid sequence shown by SEQ ID NO: 10; or the amino acid sequence shown by SEQ ID NO: 14.

* * * * *

SEQUENCE LISTING

<160> NUMBER OF SEQ ID NOS: 29

<210> SEQ ID NO 1
<211> LENGTH: 1347
<212> TYPE: DNA
<213> ORGANISM: Homo sapiens
<220> FEATURE:
<221> NAME/KEY: CDS
<222> LOCATION: (1)..(1347)

<400> SEQUENCE: 1

| | | | | | | | | | | | | | | | | |
|---|---|---|---|---|---|---|---|---|---|---|---|---|---|---|---|---|
| atg | cca | gga | ata | aaa | agg | ata | ctc | act | gtt | acc | att | ctg | gct | ctc | tgt | 48 |
| Met | Pro | Gly | Ile | Lys | Arg | Ile | Leu | Thr | Val | Thr | Ile | Leu | Ala | Leu | Cys | |
| 1 | | | | 5 | | | | | 10 | | | | | 15 | | |
| ctt | cca | agc | cct | ggg | aat | gca | cag | gca | cag | tgc | acg | aat | ggc | ttt | gac | 96 |
| Leu | Pro | Ser | Pro | Gly | Asn | Ala | Gln | Ala | Gln | Cys | Thr | Asn | Gly | Phe | Asp | |
| | | | 20 | | | | | 25 | | | | | 30 | | | |
| ctg | gat | cgc | cag | tca | gga | cag | tgt | tta | gat | att | gat | gaa | tgc | cga | acc | 144 |
| Leu | Asp | Arg | Gln | Ser | Gly | Gln | Cys | Leu | Asp | Ile | Asp | Glu | Cys | Arg | Thr | |
| | | 35 | | | | | 40 | | | | | 45 | | | | |
| atc | ccc | gag | gcc | tgc | cga | gga | gac | atg | atg | tgt | gtt | aac | caa | aat | ggc | 192 |
| Ile | Pro | Glu | Ala | Cys | Arg | Gly | Asp | Met | Met | Cys | Val | Asn | Gln | Asn | Gly | |
| 50 | | | | | 55 | | | | | 60 | | | | | | |
| ggg | tat | tta | tgc | att | ccc | cgg | aca | aac | cct | gtg | tat | cga | ggg | ccc | tac | 240 |
| Gly | Tyr | Leu | Cys | Ile | Pro | Arg | Thr | Asn | Pro | Val | Tyr | Arg | Gly | Pro | Tyr | |
| 65 | | | | | 70 | | | | | 75 | | | | | 80 | |
| tcg | aac | ccc | tac | tcg | acc | ccc | tac | tca | ggt | ccg | tac | cca | gca | gct | gcc | 288 |
| Ser | Asn | Pro | Tyr | Ser | Thr | Pro | Tyr | Ser | Gly | Pro | Tyr | Pro | Ala | Ala | Ala | |
| | | | | 85 | | | | | 90 | | | | | 95 | | |
| cca | cca | ctc | tca | gct | cca | aac | tat | ccc | acg | atc | tcc | agg | cct | ctt | ata | 336 |
| Pro | Pro | Leu | Ser | Ala | Pro | Asn | Tyr | Pro | Thr | Ile | Ser | Arg | Pro | Leu | Ile | |
| | | | 100 | | | | | 105 | | | | | 110 | | | |
| tgc | cgc | ttt | gga | tac | cag | atg | gat | gaa | agc | aac | caa | tgt | gtg | gat | gtg | 384 |
| Cys | Arg | Phe | Gly | Tyr | Gln | Met | Asp | Glu | Ser | Asn | Gln | Cys | Val | Asp | Val | |
| | | 115 | | | | | 120 | | | | | 125 | | | | |
| gac | gag | tgt | gca | aca | gat | tcc | cac | cag | tgc | aac | ccc | acc | cag | atc | tgc | 432 |
| Asp | Glu | Cys | Ala | Thr | Asp | Ser | His | Gln | Cys | Asn | Pro | Thr | Gln | Ile | Cys | |
| 130 | | | | | 135 | | | | | 140 | | | | | | |
| atc | aat | act | gaa | ggc | ggg | tac | acc | tgc | tcc | tgc | acc | gac | gga | tat | tgg | 480 |
| Ile | Asn | Thr | Glu | Gly | Gly | Tyr | Thr | Cys | Ser | Cys | Thr | Asp | Gly | Tyr | Trp | |
| 145 | | | | | 150 | | | | | 155 | | | | | 160 | |
| ctt | ctg | gaa | ggc | cag | tgc | tta | gac | att | gat | gaa | tgt | cgc | tat | ggt | tac | 528 |
| Leu | Leu | Glu | Gly | Gln | Cys | Leu | Asp | Ile | Asp | Glu | Cys | Arg | Tyr | Gly | Tyr | |
| | | | 165 | | | | | 170 | | | | | 175 | | | |
| tgc | cag | cag | ctc | tgt | gcg | aat | gtt | cct | gga | tcc | tat | tct | tgt | aca | tgc | 576 |
| Cys | Gln | Gln | Leu | Cys | Ala | Asn | Val | Pro | Gly | Ser | Tyr | Ser | Cys | Thr | Cys | |
| | | 180 | | | | | 185 | | | | | 190 | | | | |
| aac | cct | ggt | ttt | acc | ctc | aat | gag | gat | gga | agg | tct | tgc | caa | gat | gtg | 624 |
| Asn | Pro | Gly | Phe | Thr | Leu | Asn | Glu | Asp | Gly | Arg | Ser | Cys | Gln | Asp | Val | |
| | | 195 | | | | | 200 | | | | | 205 | | | | |
| aac | gag | tgt | gcc | acc | gag | aac | ccc | tgc | gtg | caa | acc | tgc | gtc | aac | acc | 672 |
| Asn | Glu | Cys | Ala | Thr | Glu | Asn | Pro | Cys | Val | Gln | Thr | Cys | Val | Asn | Thr | |
| 210 | | | | | 215 | | | | | 220 | | | | | | |
| tac | ggc | tct | ttc | atc | tgc | cgc | tgt | gac | cca | gga | tat | gaa | ctt | gag | gaa | 720 |
| Tyr | Gly | Ser | Phe | Ile | Cys | Arg | Cys | Asp | Pro | Gly | Tyr | Glu | Leu | Glu | Glu | |
| 225 | | | | | 230 | | | | | 235 | | | | | 240 | |
| gat | ggc | gtt | cat | tgc | agt | gat | atg | gac | gag | tgc | agc | ttc | tct | gag | ttc | 768 |
| Asp | Gly | Val | His | Cys | Ser | Asp | Met | Asp | Glu | Cys | Ser | Phe | Ser | Glu | Phe | |
| | | | | 245 | | | | | 250 | | | | | 255 | | |
| ctc | tgc | caa | cat | gag | tgt | gtg | aac | cag | ccc | ggc | aca | tac | ttc | tgc | tcc | 816 |

```
                                                                         -continued
Leu Cys Gln His Glu Cys Val Asn Gln Pro Gly Thr Tyr Phe Cys Ser
            260                 265                 270 tgc cct cca ggc tac atc ctg ctg gat gac aac cga agc tgc caa gac         864
Cys Pro Pro Gly Tyr Ile Leu Leu Asp Asp Asn Arg Ser Cys Gln Asp
        275                 280                 285 atc aac gaa tgt gag cac agg aac cac acg tgc aac ctg cag cag acg         912
Ile Asn Glu Cys Glu His Arg Asn His Thr Cys Asn Leu Gln Gln Thr
    290                 295                 300 tgc tac aat tta caa ggg ggc ttc aaa tgc atc gac ccc atc cgc tgt         960
Cys Tyr Asn Leu Gln Gly Gly Phe Lys Cys Ile Asp Pro Ile Arg Cys
305                 310                 315                 320 gag gag cct tat ctg agg atc agt gat aac cgc tgt atg tgt cct gct        1008
Glu Glu Pro Tyr Leu Arg Ile Ser Asp Asn Arg Cys Met Cys Pro Ala
                325                 330                 335 gag aac cct ggc tgc aga gac cag ccc ttt acc atc ttg tac cgg gac        1056
Glu Asn Pro Gly Cys Arg Asp Gln Pro Phe Thr Ile Leu Tyr Arg Asp
            340                 345                 350 atg gac gtg gtg tca gga cgc tcc gtt ccc gct gac atc ttc caa atg        1104
Met Asp Val Val Ser Gly Arg Ser Val Pro Ala Asp Ile Phe Gln Met
        355                 360                 365 caa gcc acg acc cgc tac cct ggg gcc tat tac att ttc cag atc aaa        1152
Gln Ala Thr Thr Arg Tyr Pro Gly Ala Tyr Tyr Ile Phe Gln Ile Lys
    370                 375                 380 tct ggg aat gag ggc aga gaa ttt tac atg cgg caa acg ggc ccc atc        1200
Ser Gly Asn Glu Gly Arg Glu Phe Tyr Met Arg Gln Thr Gly Pro Ile
385                 390                 395                 400 agt gcc acc ctg gtg atg aca cgc ccc atc aaa ggg ccc cgg gaa atc        1248
Ser Ala Thr Leu Val Met Thr Arg Pro Ile Lys Gly Pro Arg Glu Ile
                405                 410                 415 cag ctg gac ttg gaa atg atc act gtc aac act gtc atc aac ttc aga        1296
Gln Leu Asp Leu Glu Met Ile Thr Val Asn Thr Val Ile Asn Phe Arg
            420                 425                 430 ggc agc tcc gtg atc cga ctg cgg ata tat gtg tcg cag tac cca ttc        1344
Gly Ser Ser Val Ile Arg Leu Arg Ile Tyr Val Ser Gln Tyr Pro Phe
        435                 440                 445 tga                                                                    1347

<210> SEQ ID NO 2
<211> LENGTH: 448
<212> TYPE: PRT
<213> ORGANISM: Homo sapiens

<400> SEQUENCE: 2

Met Pro Gly Ile Lys Arg Ile Leu Thr Val Thr Ile Leu Ala Leu Cys
1               5                   10                  15

Leu Pro Ser Pro Gly Asn Ala Gln Ala Gln Cys Thr Asn Gly Phe Asp
            20                  25                  30

Leu Asp Arg Gln Ser Gly Gln Cys Leu Asp Ile Asp Glu Cys Arg Thr
        35                  40                  45

Ile Pro Glu Ala Cys Arg Gly Asp Met Met Cys Val Asn Gln Asn Gly
    50                  55                  60

Gly Tyr Leu Cys Ile Pro Arg Thr Asn Pro Val Tyr Arg Gly Pro Tyr
65                  70                  75                  80

Ser Asn Pro Tyr Ser Thr Pro Tyr Ser Gly Pro Tyr Pro Ala Ala Ala
                85                  90                  95

Pro Pro Leu Ser Ala Pro Asn Tyr Pro Thr Ile Ser Arg Pro Leu Ile
            100                 105                 110

Cys Arg Phe Gly Tyr Gln Met Asp Glu Ser Asn Gln Cys Val Asp Val
        115                 120                 125
```

```
Asp Glu Cys Ala Thr Asp Ser His Gln Cys Asn Pro Thr Gln Ile Cys
        130                 135                 140

Ile Asn Thr Glu Gly Gly Tyr Thr Cys Ser Cys Thr Asp Gly Tyr Trp
145                 150                 155                 160

Leu Leu Glu Gly Gln Cys Leu Asp Ile Asp Glu Cys Arg Tyr Gly Tyr
                165                 170                 175

Cys Gln Gln Leu Cys Ala Asn Val Pro Gly Ser Tyr Ser Cys Thr Cys
            180                 185                 190

Asn Pro Gly Phe Thr Leu Asn Glu Asp Gly Arg Ser Cys Gln Asp Val
        195                 200                 205

Asn Glu Cys Ala Thr Glu Asn Pro Cys Val Gln Thr Cys Val Asn Thr
    210                 215                 220

Tyr Gly Ser Phe Ile Cys Arg Cys Asp Pro Gly Tyr Glu Leu Glu Glu
225                 230                 235                 240

Asp Gly Val His Cys Ser Asp Met Asp Glu Cys Ser Phe Ser Glu Phe
                245                 250                 255

Leu Cys Gln His Glu Cys Val Asn Gln Pro Gly Thr Tyr Phe Cys Ser
            260                 265                 270

Cys Pro Pro Gly Tyr Ile Leu Leu Asp Asp Asn Arg Ser Cys Gln Asp
        275                 280                 285

Ile Asn Glu Cys Glu His Arg Asn His Thr Cys Asn Leu Gln Gln Thr
    290                 295                 300

Cys Tyr Asn Leu Gln Gly Gly Phe Lys Cys Ile Asp Pro Ile Arg Cys
305                 310                 315                 320

Glu Glu Pro Tyr Leu Arg Ile Ser Asp Asn Arg Cys Met Cys Pro Ala
                325                 330                 335

Glu Asn Pro Gly Cys Arg Asp Gln Pro Phe Thr Ile Leu Tyr Arg Asp
            340                 345                 350

Met Asp Val Val Ser Gly Arg Ser Val Pro Ala Asp Ile Phe Gln Met
        355                 360                 365

Gln Ala Thr Thr Arg Tyr Pro Gly Ala Tyr Tyr Ile Phe Gln Ile Lys
    370                 375                 380

Ser Gly Asn Glu Gly Arg Glu Phe Tyr Met Arg Gln Thr Gly Pro Ile
385                 390                 395                 400

Ser Ala Thr Leu Val Met Thr Arg Pro Ile Lys Gly Pro Arg Glu Ile
                405                 410                 415

Gln Leu Asp Leu Glu Met Ile Thr Val Asn Thr Val Ile Asn Phe Arg
            420                 425                 430

Gly Ser Ser Val Ile Arg Leu Arg Ile Tyr Val Ser Gln Tyr Pro Phe
        435                 440                 445

<210> SEQ ID NO 3
<211> LENGTH: 1278
<212> TYPE: DNA
<213> ORGANISM: Homo sapiens
<220> FEATURE:
<221> NAME/KEY: CDS
<222> LOCATION: (1)..(1278)

<400> SEQUENCE: 3 cag gca cag tgc acg aat ggc ttt gac ctg gat cgc cag tca gga cag      48
Gln Ala Gln Cys Thr Asn Gly Phe Asp Leu Asp Arg Gln Ser Gly Gln
1               5                   10                  15 tgt tta gat att gat gaa tgc cga acc atc ccc gag gcc tgc cga gga      96
Cys Leu Asp Ile Asp Glu Cys Arg Thr Ile Pro Glu Ala Cys Arg Gly
            20                  25                  30
```

```
gac atg atg tgt gtt aac caa aat ggc ggg tat tta tgc att ccc cgg      144
Asp Met Met Cys Val Asn Gln Asn Gly Gly Tyr Leu Cys Ile Pro Arg
         35              40              45 aca aac cct gtg tat cga ggg ccc tac tcg aac ccc tac tcg acc ccc      192
Thr Asn Pro Val Tyr Arg Gly Pro Tyr Ser Asn Pro Tyr Ser Thr Pro
 50              55              60 tac tca ggt ccg tac cca gca gct gcc cca cca ctc tca gct cca aac      240
Tyr Ser Gly Pro Tyr Pro Ala Ala Ala Pro Pro Leu Ser Ala Pro Asn
 65              70              75              80 tat ccc acg atc tcc agg cct ctt ata tgc cgc ttt gga tac cag atg      288
Tyr Pro Thr Ile Ser Arg Pro Leu Ile Cys Arg Phe Gly Tyr Gln Met
             85              90              95 gat gaa agc aac caa tgt gtg gat gtg gac gag tgt gca aca gat tcc      336
Asp Glu Ser Asn Gln Cys Val Asp Val Asp Glu Cys Ala Thr Asp Ser
                100             105             110 cac cag tgc aac ccc acc cag atc tgc atc aat act gaa ggc ggg tac      384
His Gln Cys Asn Pro Thr Gln Ile Cys Ile Asn Thr Glu Gly Gly Tyr
        115             120             125 acc tgc tcc tgc acc gac gga tat tgg ctt ctg gaa ggc cag tgc tta      432
Thr Cys Ser Cys Thr Asp Gly Tyr Trp Leu Leu Glu Gly Gln Cys Leu
130             135             140 gac att gat gaa tgt cgc tat ggt tac tgc cag cag ctc tgt gcg aat      480
Asp Ile Asp Glu Cys Arg Tyr Gly Tyr Cys Gln Gln Leu Cys Ala Asn
145             150             155             160 gtt cct gga tcc tat tct tgt aca tgc aac cct ggt ttt acc ctc aat      528
Val Pro Gly Ser Tyr Ser Cys Thr Cys Asn Pro Gly Phe Thr Leu Asn
                165             170             175 gag gat gga agg tct tgc caa gat gtg aac gag tgt gcc acc gag aac      576
Glu Asp Gly Arg Ser Cys Gln Asp Val Asn Glu Cys Ala Thr Glu Asn
            180             185             190 ccc tgc gtg caa acc tgc gtc aac acc tac ggc tct ttc atc tgc cgc      624
Pro Cys Val Gln Thr Cys Val Asn Thr Tyr Gly Ser Phe Ile Cys Arg
        195             200             205 tgt gac cca gga tat gaa ctt gag gaa gat ggc gtt cat tgc agt gat      672
Cys Asp Pro Gly Tyr Glu Leu Glu Glu Asp Gly Val His Cys Ser Asp
210             215             220 atg gac gag tgc agc ttc tct gag ttc ctc tgc caa cat gag tgt gtg      720
Met Asp Glu Cys Ser Phe Ser Glu Phe Leu Cys Gln His Glu Cys Val
225             230             235             240 aac cag ccc ggc aca tac ttc tgc tcc tgc cct cca ggc tac atc ctg      768
Asn Gln Pro Gly Thr Tyr Phe Cys Ser Cys Pro Pro Gly Tyr Ile Leu
                245             250             255 ctg gat gac aac cga agc tgc caa gac atc aac gaa tgt gag cac agg      816
Leu Asp Asp Asn Arg Ser Cys Gln Asp Ile Asn Glu Cys Glu His Arg
            260             265             270 aac cac acg tgc aac ctg cag cag acg tgc tac aat tta caa ggg ggc      864
Asn His Thr Cys Asn Leu Gln Gln Thr Cys Tyr Asn Leu Gln Gly Gly
        275             280             285 ttc aaa tgc atc gac ccc atc cgc tgt gag gag cct tat ctg agg atc      912
Phe Lys Cys Ile Asp Pro Ile Arg Cys Glu Glu Pro Tyr Leu Arg Ile
290             295             300 agt gat aac cgc tgt atg tgt cct gct gag aac cct ggc tgc aga gac      960
Ser Asp Asn Arg Cys Met Cys Pro Ala Glu Asn Pro Gly Cys Arg Asp
305             310             315             320 cag ccc ttt acc atc ttg tac cgg gac atg gac gtg gtg tca gga cgc     1008
Gln Pro Phe Thr Ile Leu Tyr Arg Asp Met Asp Val Val Ser Gly Arg
                325             330             335 tcc gtt ccc gct gac atc ttc caa atg caa gcc acg acc cgc tac cct     1056
Ser Val Pro Ala Asp Ile Phe Gln Met Gln Ala Thr Thr Arg Tyr Pro
            340             345             350
```

-continued

| | | | | | | | | | | | | | | | |
|---|---|---|---|---|---|---|---|---|---|---|---|---|---|---|---|
| ggg | gcc | tat | tac | att | ttc | cag | atc | aaa | tct | ggg | aat | gag | ggc | aga | gaa | 1104
| Gly | Ala | Tyr | Tyr | Ile | Phe | Gln | Ile | Lys | Ser | Gly | Asn | Glu | Gly | Arg | Glu |
| | | 355 | | | | 360 | | | | 365 | | | | | |

| ttt | tac | atg | cgg | caa | acg | ggc | ccc | atc | agt | gcc | acc | ctg | gtg | atg | aca | 1152
| Phe | Tyr | Met | Arg | Gln | Thr | Gly | Pro | Ile | Ser | Ala | Thr | Leu | Val | Met | Thr |
| 370 | | | | | 375 | | | | | 380 | | | | | |

| cgc | ccc | atc | aaa | ggg | ccc | cgg | gaa | atc | cag | ctg | gac | ttg | gaa | atg | atc | 1200
| Arg | Pro | Ile | Lys | Gly | Pro | Arg | Glu | Ile | Gln | Leu | Asp | Leu | Glu | Met | Ile |
| 385 | | | | 390 | | | | | 395 | | | | | 400 | |

| act | gtc | aac | act | gtc | atc | aac | ttc | aga | ggc | agc | tcc | gtg | atc | cga | ctg | 1248
| Thr | Val | Asn | Thr | Val | Ile | Asn | Phe | Arg | Gly | Ser | Ser | Val | Ile | Arg | Leu |
| | | | 405 | | | | | 410 | | | | | 415 | | |

| cgg | ata | tat | gtg | tcg | cag | tac | cca | ttc | tga | | | | | | | 1278
| Arg | Ile | Tyr | Val | Ser | Gln | Tyr | Pro | Phe | | | | | | | |
| | 420 | | | | | 425 | | | | | | | | | |

<210> SEQ ID NO 4
<211> LENGTH: 425
<212> TYPE: PRT
<213> ORGANISM: Homo sapiens

<400> SEQUENCE: 4

Gln Ala Gln Cys Thr Asn Gly Phe Asp Leu Asp Arg Gln Ser Gly Gln
1               5                  10                  15

Cys Leu Asp Ile Asp Glu Cys Arg Thr Ile Pro Glu Ala Cys Arg Gly
            20                  25                  30

Asp Met Met Cys Val Asn Gln Asn Gly Gly Tyr Leu Cys Ile Pro Arg
        35                  40                  45

Thr Asn Pro Val Tyr Arg Gly Pro Tyr Ser Asn Pro Tyr Ser Thr Pro
    50                  55                  60

Tyr Ser Gly Pro Tyr Pro Ala Ala Pro Pro Leu Ser Ala Pro Asn
65                  70                  75                  80

Tyr Pro Thr Ile Ser Arg Pro Leu Ile Cys Arg Phe Gly Tyr Gln Met
                85                  90                  95

Asp Glu Ser Asn Gln Cys Val Asp Val Asp Glu Cys Ala Thr Asp Ser
            100                 105                 110

His Gln Cys Asn Pro Thr Gln Ile Cys Ile Asn Thr Glu Gly Gly Tyr
        115                 120                 125

Thr Cys Ser Cys Thr Asp Gly Tyr Trp Leu Leu Glu Gly Gln Cys Leu
    130                 135                 140

Asp Ile Asp Glu Cys Arg Tyr Gly Tyr Cys Gln Gln Leu Cys Ala Asn
145                 150                 155                 160

Val Pro Gly Ser Tyr Ser Cys Thr Cys Asn Pro Gly Phe Thr Leu Asn
                165                 170                 175

Glu Asp Gly Arg Ser Cys Gln Asp Val Asn Glu Cys Ala Thr Glu Asn
            180                 185                 190

Pro Cys Val Gln Thr Cys Val Asn Thr Tyr Gly Ser Phe Ile Cys Arg
        195                 200                 205

Cys Asp Pro Gly Tyr Glu Leu Glu Glu Asp Gly Val His Cys Ser Asp
    210                 215                 220

Met Asp Glu Cys Ser Phe Ser Glu Phe Leu Cys Gln His Glu Cys Val
225                 230                 235                 240

Asn Gln Pro Gly Thr Tyr Phe Cys Ser Cys Pro Pro Gly Tyr Ile Leu
                245                 250                 255

Leu Asp Asp Asn Arg Ser Cys Gln Asp Ile Asn Glu Cys Glu His Arg
            260                 265                 270

Asn His Thr Cys Asn Leu Gln Gln Thr Cys Tyr Asn Leu Gln Gly Gly

```
                275                 280                 285
Phe Lys Cys Ile Asp Pro Ile Arg Cys Glu Glu Pro Tyr Leu Arg Ile
290                 295                 300

Ser Asp Asn Arg Cys Met Cys Pro Ala Glu Asn Pro Gly Cys Arg Asp
305                 310                 315                 320

Gln Pro Phe Thr Ile Leu Tyr Arg Asp Met Asp Val Val Ser Gly Arg
                325                 330                 335

Ser Val Pro Ala Asp Ile Phe Gln Met Gln Ala Thr Thr Arg Tyr Pro
                340                 345                 350

Gly Ala Tyr Tyr Ile Phe Gln Ile Lys Ser Gly Asn Glu Gly Arg Glu
                355                 360                 365

Phe Tyr Met Arg Gln Thr Gly Pro Ile Ser Ala Thr Leu Val Met Thr
370                 375                 380

Arg Pro Ile Lys Gly Pro Arg Glu Ile Gln Leu Asp Leu Glu Met Ile
385                 390                 395                 400

Thr Val Asn Thr Val Ile Asn Phe Arg Gly Ser Ser Val Ile Arg Leu
                405                 410                 415

Arg Ile Tyr Val Ser Gln Tyr Pro Phe
                420                 425

<210> SEQ ID NO 5
<211> LENGTH: 162
<212> TYPE: DNA
<213> ORGANISM: Homo sapiens
<220> FEATURE:
<221> NAME/KEY: CDS
<222> LOCATION: (1)..(162)

<400> SEQUENCE: 5 cag gca cag tgc acg aat ggc ttt gac ctg gat cgc cag tca gga cag      48
Gln Ala Gln Cys Thr Asn Gly Phe Asp Leu Asp Arg Gln Ser Gly Gln
1               5                   10                  15 tgt tta gat att gat gaa tgc cga acc atc ccc gag gcc tgc cga gga      96
Cys Leu Asp Ile Asp Glu Cys Arg Thr Ile Pro Glu Ala Cys Arg Gly
            20                  25                  30 gac atg atg tgt gtt aac caa aat ggc ggg tat tta tgc att ccc cgg     144
Asp Met Met Cys Val Asn Gln Asn Gly Gly Tyr Leu Cys Ile Pro Arg
        35                  40                  45 aca aac cct gtg tat cga                                             162
Thr Asn Pro Val Tyr Arg
    50

<210> SEQ ID NO 6
<211> LENGTH: 54
<212> TYPE: PRT
<213> ORGANISM: Homo sapiens

<400> SEQUENCE: 6

Gln Ala Gln Cys Thr Asn Gly Phe Asp Leu Asp Arg Gln Ser Gly Gln
1               5                   10                  15

Cys Leu Asp Ile Asp Glu Cys Arg Thr Ile Pro Glu Ala Cys Arg Gly
            20                  25                  30

Asp Met Met Cys Val Asn Gln Asn Gly Gly Tyr Leu Cys Ile Pro Arg
        35                  40                  45

Thr Asn Pro Val Tyr Arg
    50

<210> SEQ ID NO 7
<211> LENGTH: 1116
<212> TYPE: DNA
```

```
<213> ORGANISM: Homo sapiens
<220> FEATURE:
<221> NAME/KEY: CDS
<222> LOCATION: (1)..(1116)

<400> SEQUENCE: 7 ggg ccc tac tcg aac ccc tac tcg acc ccc tac tca ggt ccg tac cca        48
Gly Pro Tyr Ser Asn Pro Tyr Ser Thr Pro Tyr Ser Gly Pro Tyr Pro
 1               5                  10                  15 gca gct gcc cca cca ctc tca gct cca aac tat ccc acg atc tcc agg        96
Ala Ala Ala Pro Pro Leu Ser Ala Pro Asn Tyr Pro Thr Ile Ser Arg
             20                  25                  30 cct ctt ata tgc cgc ttt gga tac cag atg gat gaa agc aac caa tgt       144
Pro Leu Ile Cys Arg Phe Gly Tyr Gln Met Asp Glu Ser Asn Gln Cys
         35                  40                  45 gtg gat gtg gac gag tgt gca aca gat tcc cac cag tgc aac ccc acc       192
Val Asp Val Asp Glu Cys Ala Thr Asp Ser His Gln Cys Asn Pro Thr
 50                  55                  60 cag atc tgc atc aat act gaa ggc ggg tac acc tgc tcc tgc acc gac       240
Gln Ile Cys Ile Asn Thr Glu Gly Gly Tyr Thr Cys Ser Cys Thr Asp
 65                  70                  75                  80 gga tat tgg ctt ctg gaa ggc cag tgc tta gac att gat gaa tgt cgc       288
Gly Tyr Trp Leu Leu Glu Gly Gln Cys Leu Asp Ile Asp Glu Cys Arg
                 85                  90                  95 tat ggt tac tgc cag cag ctc tgt gcg aat gtt cct gga tcc tat tct       336
Tyr Gly Tyr Cys Gln Gln Leu Cys Ala Asn Val Pro Gly Ser Tyr Ser
            100                 105                 110 tgt aca tgc aac cct ggt ttt acc ctc aat gag gat gga agg tct tgc       384
Cys Thr Cys Asn Pro Gly Phe Thr Leu Asn Glu Asp Gly Arg Ser Cys
        115                 120                 125 caa gat gtg aac gag tgt gcc acc gag aac ccc tgc gtg caa acc tgc       432
Gln Asp Val Asn Glu Cys Ala Thr Glu Asn Pro Cys Val Gln Thr Cys
    130                 135                 140 gtc aac acc tac ggc tct ttc atc tgc cgc tgt gac cca gga tat gaa       480
Val Asn Thr Tyr Gly Ser Phe Ile Cys Arg Cys Asp Pro Gly Tyr Glu
145                 150                 155                 160 ctt gag gaa gat ggc gtt cat tgc agt gat atg gac gag tgc agc ttc       528
Leu Glu Glu Asp Gly Val His Cys Ser Asp Met Asp Glu Cys Ser Phe
                165                 170                 175 tct gag ttc ctc tgc caa cat gag tgt gtg aac cag ccc ggc aca tac       576
Ser Glu Phe Leu Cys Gln His Glu Cys Val Asn Gln Pro Gly Thr Tyr
            180                 185                 190 ttc tgc tcc tgc cct cca ggc tac atc ctg ctg gat gac aac cga agc       624
Phe Cys Ser Cys Pro Pro Gly Tyr Ile Leu Leu Asp Asp Asn Arg Ser
        195                 200                 205 tgc caa gac atc aac gaa tgt gag cac agg aac cac acg tgc aac ctg       672
Cys Gln Asp Ile Asn Glu Cys Glu His Arg Asn His Thr Cys Asn Leu
    210                 215                 220 cag cag acg tgc tac aat tta caa ggg ggc ttc aaa tgc atc gac ccc       720
Gln Gln Thr Cys Tyr Asn Leu Gln Gly Gly Phe Lys Cys Ile Asp Pro
225                 230                 235                 240 atc cgc tgt gag gag cct tat ctg agg atc agt gat aac cgc tgt atg       768
Ile Arg Cys Glu Glu Pro Tyr Leu Arg Ile Ser Asp Asn Arg Cys Met
                245                 250                 255 tgt cct gct gag aac cct ggc tgc aga gac cag ccc ttt acc atc ttg       816
Cys Pro Ala Glu Asn Pro Gly Cys Arg Asp Gln Pro Phe Thr Ile Leu
            260                 265                 270 tac cgg gac atg gac gtg gtg tca gga cgc tcc gtt ccc gct gac atc       864
Tyr Arg Asp Met Asp Val Val Ser Gly Arg Ser Val Pro Ala Asp Ile
        275                 280                 285 ttc caa atg caa gcc acg acc cgc tac cct ggg gcc tat tac att ttc       912
```

```
                                                                        960
cag atc aaa tct ggg aat gag ggc aga gaa ttt tac atg cgg caa acg
Gln Ile Lys Ser Gly Asn Glu Gly Arg Glu Phe Tyr Met Arg Gln Thr
305             310                 315                 320

1008
ggc ccc atc agt gcc acc ctg gtg atg aca cgc ccc atc aaa ggg ccc
Gly Pro Ile Ser Ala Thr Leu Val Met Thr Arg Pro Ile Lys Gly Pro
            325                 330                 335

1056
cgg gaa atc cag ctg gac ttg gaa atg atc act gtc aac act gtc atc
Arg Glu Ile Gln Leu Asp Leu Glu Met Ile Thr Val Asn Thr Val Ile
        340                 345                 350

1104
aac ttc aga ggc agc tcc gtg atc cga ctg cgg ata tat gtg tcg cag
Asn Phe Arg Gly Ser Ser Val Ile Arg Leu Arg Ile Tyr Val Ser Gln
    355                 360                 365

1116
tac cca ttc tga
Tyr Pro Phe
    370

<210> SEQ ID NO 8
<211> LENGTH: 371
<212> TYPE: PRT
<213> ORGANISM: Homo sapiens

<400> SEQUENCE: 8

Gly Pro Tyr Ser Asn Pro Tyr Ser Thr Pro Tyr Ser Gly Pro Tyr Pro
1               5                   10                  15

Ala Ala Ala Pro Pro Leu Ser Ala Pro Asn Tyr Pro Thr Ile Ser Arg
            20                  25                  30

Pro Leu Ile Cys Arg Phe Gly Tyr Gln Met Asp Glu Ser Asn Gln Cys
        35                  40                  45

Val Asp Val Asp Glu Cys Ala Thr Asp Ser His Gln Cys Asn Pro Thr
50                  55                  60

Gln Ile Cys Ile Asn Thr Glu Gly Gly Tyr Thr Cys Ser Cys Thr Asp
65                  70                  75                  80

Gly Tyr Trp Leu Leu Glu Gly Gln Cys Leu Asp Ile Asp Glu Cys Arg
                85                  90                  95

Tyr Gly Tyr Cys Gln Gln Leu Cys Ala Asn Val Pro Gly Ser Tyr Ser
            100                 105                 110

Cys Thr Cys Asn Pro Gly Phe Thr Leu Asn Glu Asp Gly Arg Ser Cys
        115                 120                 125

Gln Asp Val Asn Glu Cys Ala Thr Glu Asn Pro Cys Val Gln Thr Cys
    130                 135                 140

Val Asn Thr Tyr Gly Ser Phe Ile Cys Arg Cys Asp Pro Gly Tyr Glu
145                 150                 155                 160

Leu Glu Glu Asp Gly Val His Cys Ser Asp Met Asp Glu Cys Ser Phe
                165                 170                 175

Ser Glu Phe Leu Cys Gln His Glu Cys Val Asn Gln Pro Gly Thr Tyr
            180                 185                 190

Phe Cys Ser Cys Pro Pro Gly Tyr Ile Leu Leu Asp Asp Asn Arg Ser
        195                 200                 205

Cys Gln Asp Ile Asn Glu Cys Glu His Arg Asn His Thr Cys Asn Leu
    210                 215                 220

Gln Gln Thr Cys Tyr Asn Leu Gln Gly Gly Phe Lys Cys Ile Asp Pro
225                 230                 235                 240

Ile Arg Cys Glu Glu Pro Tyr Leu Arg Ile Ser Asp Asn Arg Cys Met
                245                 250                 255

Cys Pro Ala Glu Asn Pro Gly Cys Arg Asp Gln Pro Phe Thr Ile Leu
```

```
                        260                 265                 270
Tyr Arg Asp Met Asp Val Val Ser Gly Arg Ser Val Pro Ala Asp Ile
                275                 280                 285

Phe Gln Met Gln Ala Thr Thr Arg Tyr Pro Gly Ala Tyr Tyr Ile Phe
            290                 295                 300

Gln Ile Lys Ser Gly Asn Glu Gly Arg Glu Phe Tyr Met Arg Gln Thr
305                 310                 315                 320

Gly Pro Ile Ser Ala Thr Leu Val Met Thr Arg Pro Ile Lys Gly Pro
                325                 330                 335

Arg Glu Ile Gln Leu Asp Leu Glu Met Ile Thr Val Asn Thr Val Ile
            340                 345                 350

Asn Phe Arg Gly Ser Ser Val Ile Arg Leu Arg Ile Tyr Val Ser Gln
                355                 360                 365

Tyr Pro Phe
    370

<210> SEQ ID NO 9
<211> LENGTH: 162
<212> TYPE: DNA
<213> ORGANISM: Mus musculus
<220> FEATURE:
<221> NAME/KEY: CDS
<222> LOCATION: (1)..(162)

<400> SEQUENCE: 9 cag cag cag tgc aca aac ggc ttt gac ctg gac cgc cag tca gga cag      48
Gln Gln Gln Cys Thr Asn Gly Phe Asp Leu Asp Arg Gln Ser Gly Gln
1               5                   10                  15 tgt cta gat att gat gaa tgc cgg acc atc cct gag gct tgt cgt ggg      96
Cys Leu Asp Ile Asp Glu Cys Arg Thr Ile Pro Glu Ala Cys Arg Gly
                20                  25                  30 gac atg atg tgt gtc aac cag aat ggc ggg tat ttg tgc atc cct cga     144
Asp Met Met Cys Val Asn Gln Asn Gly Gly Tyr Leu Cys Ile Pro Arg
            35                  40                  45 acc aac cca gtg tat cga                                             162
Thr Asn Pro Val Tyr Arg
    50

<210> SEQ ID NO 10
<211> LENGTH: 54
<212> TYPE: PRT
<213> ORGANISM: Mus musculus

<400> SEQUENCE: 10

Gln Gln Gln Cys Thr Asn Gly Phe Asp Leu Asp Arg Gln Ser Gly Gln
1               5                   10                  15

Cys Leu Asp Ile Asp Glu Cys Arg Thr Ile Pro Glu Ala Cys Arg Gly
                20                  25                  30

Asp Met Met Cys Val Asn Gln Asn Gly Gly Tyr Leu Cys Ile Pro Arg
            35                  40                  45

Thr Asn Pro Val Tyr Arg
    50

<210> SEQ ID NO 11
<211> LENGTH: 1113
<212> TYPE: DNA
<213> ORGANISM: Mus musculus
<220> FEATURE:
<221> NAME/KEY: CDS
<222> LOCATION: (1)..(1113)

<400> SEQUENCE: 11
```

```
ggg cct tac tca aat ccc tac tct aca tcc tac tca ggc cca tac cca      48
Gly Pro Tyr Ser Asn Pro Tyr Ser Thr Ser Tyr Ser Gly Pro Tyr Pro
1               5                   10                  15 gca gcg gcc cca cca gta cca gct tcc aac tac ccc acg att tca agg      96
Ala Ala Ala Pro Pro Val Pro Ala Ser Asn Tyr Pro Thr Ile Ser Arg
            20                  25                  30 cct ctt gtc tgc cgc ttt ggg tat cag atg gat gaa ggc aac cag tgt     144
Pro Leu Val Cys Arg Phe Gly Tyr Gln Met Asp Glu Gly Asn Gln Cys
            35                  40                  45 gtg gat gtg gac gag tgt gca aca gac tca cac cag tgc aac cct acc     192
Val Asp Val Asp Glu Cys Ala Thr Asp Ser His Gln Cys Asn Pro Thr
50                  55                  60 cag atc tgt atc aac act gaa gga ggt tac acc tgc tcc tgc acc gat     240
Gln Ile Cys Ile Asn Thr Glu Gly Gly Tyr Thr Cys Ser Cys Thr Asp
65                  70                  75                  80 ggg tac tgg ctt ctg gaa ggg cag tgc cta gat att gat gaa tgt cgc     288
Gly Tyr Trp Leu Leu Glu Gly Gln Cys Leu Asp Ile Asp Glu Cys Arg
                85                  90                  95 tat ggt tac tgc cag cag ctc tgt gca aat gtt cca gga tcc tat tcc     336
Tyr Gly Tyr Cys Gln Gln Leu Cys Ala Asn Val Pro Gly Ser Tyr Ser
                100                 105                 110 tgt aca tgc aac cct ggt ttc acc ctc aac gac gat gga agg tct tgc     384
Cys Thr Cys Asn Pro Gly Phe Thr Leu Asn Asp Asp Gly Arg Ser Cys
            115                 120                 125 caa gat gtg aac gag tgc gaa act gag aat ccc tgt gtt cag acc tgt     432
Gln Asp Val Asn Glu Cys Glu Thr Glu Asn Pro Cys Val Gln Thr Cys
130                 135                 140 gtc aac acc tat ggc tct ttc atc tgc cgc tgt gac cca gga tat gaa     480
Val Asn Thr Tyr Gly Ser Phe Ile Cys Arg Cys Asp Pro Gly Tyr Glu
145                 150                 155                 160 ctt gag gaa gat ggc att cac tgc agt gat atg gac gag tgc agc ttc     528
Leu Glu Glu Asp Gly Ile His Cys Ser Asp Met Asp Glu Cys Ser Phe
                165                 170                 175 tcc gag ttc ctc tgt caa cac gag tgt gtg aac cag ccg ggc tca tac     576
Ser Glu Phe Leu Cys Gln His Glu Cys Val Asn Gln Pro Gly Ser Tyr
            180                 185                 190 ttc tgc tcg tgc cct cca ggc tac gtc ctg ttg gat gat aac cga agc     624
Phe Cys Ser Cys Pro Pro Gly Tyr Val Leu Leu Asp Asp Asn Arg Ser
            195                 200                 205 tgc cag gat atc aat gaa tgt gag cac cga aac cac acg tgt acc tca     672
Cys Gln Asp Ile Asn Glu Cys Glu His Arg Asn His Thr Cys Thr Ser
210                 215                 220 ctg cag act tgc tac aat cta caa ggg ggc ttc aaa tgt att gat ccc     720
Leu Gln Thr Cys Tyr Asn Leu Gln Gly Gly Phe Lys Cys Ile Asp Pro
225                 230                 235                 240 atc agc tgt gag gag cct tat ctg ctg att ggt gaa aac cgc tgt atg     768
Ile Ser Cys Glu Glu Pro Tyr Leu Leu Ile Gly Glu Asn Arg Cys Met
                245                 250                 255 tgt cct gct gag cac acc agc tgc aga gac cag cca ttc acc atc ctg     816
Cys Pro Ala Glu His Thr Ser Cys Arg Asp Gln Pro Phe Thr Ile Leu
            260                 265                 270 tat cgg gac atg gat gtg gtg tca gga cgc tcc gtt cct gct gac atc     864
Tyr Arg Asp Met Asp Val Val Ser Gly Arg Ser Val Pro Ala Asp Ile
            275                 280                 285 ttc cag atg caa gca aca acc cga tac cct ggt gcc tat tac att ttc     912
Phe Gln Met Gln Ala Thr Thr Arg Tyr Pro Gly Ala Tyr Tyr Ile Phe
            290                 295                 300 cag atc aaa tct ggc aac gag ggt cga gag ttc tat atg cgg caa aca     960
Gln Ile Lys Ser Gly Asn Glu Gly Arg Glu Phe Tyr Met Arg Gln Thr
305                 310                 315                 320
```

```
ggg cct atc agt gcc acc ctg gtg atg aca cgc ccc atc aaa ggg cct    1008
Gly Pro Ile Ser Ala Thr Leu Val Met Thr Arg Pro Ile Lys Gly Pro
            325                 330                 335 cgg gac atc cag ctg gac ttg gag atg atc act gtc aac act gtc atc    1056
Arg Asp Ile Gln Leu Asp Leu Glu Met Ile Thr Val Asn Thr Val Ile
        340                 345                 350 aac ttc aga ggc agc tcc gtg atc cga ctg cgg ata tat gtg tcg cag    1104
Asn Phe Arg Gly Ser Ser Val Ile Arg Leu Arg Ile Tyr Val Ser Gln
    355                 360                 365 tat ccg ttc                                                        1113
Tyr Pro Phe
    370

<210> SEQ ID NO 12
<211> LENGTH: 371
<212> TYPE: PRT
<213> ORGANISM: Mus musculus

<400> SEQUENCE: 12

Gly Pro Tyr Ser Asn Pro Tyr Ser Thr Ser Tyr Ser Gly Pro Tyr Pro
1               5                   10                  15

Ala Ala Ala Pro Pro Val Pro Ala Ser Asn Tyr Pro Thr Ile Ser Arg
            20                  25                  30

Pro Leu Val Cys Arg Phe Gly Tyr Gln Met Asp Glu Gly Asn Gln Cys
        35                  40                  45

Val Asp Val Asp Glu Cys Ala Thr Asp Ser His Gln Cys Asn Pro Thr
    50                  55                  60

Gln Ile Cys Ile Asn Thr Glu Gly Gly Tyr Thr Cys Ser Cys Thr Asp
65                  70                  75                  80

Gly Tyr Trp Leu Leu Glu Gly Gln Cys Leu Asp Ile Asp Glu Cys Arg
                85                  90                  95

Tyr Gly Tyr Cys Gln Gln Leu Cys Ala Asn Val Pro Gly Ser Tyr Ser
            100                 105                 110

Cys Thr Cys Asn Pro Gly Phe Thr Leu Asn Asp Asp Gly Arg Ser Cys
        115                 120                 125

Gln Asp Val Asn Glu Cys Glu Thr Glu Asn Pro Cys Val Gln Thr Cys
    130                 135                 140

Val Asn Thr Tyr Gly Ser Phe Ile Cys Arg Cys Asp Pro Gly Tyr Glu
145                 150                 155                 160

Leu Glu Glu Asp Gly Ile His Cys Ser Asp Met Asp Glu Cys Ser Phe
                165                 170                 175

Ser Glu Phe Leu Cys Gln His Glu Cys Val Asn Gln Pro Gly Ser Tyr
            180                 185                 190

Phe Cys Ser Cys Pro Pro Gly Tyr Val Leu Leu Asp Asp Asn Arg Ser
        195                 200                 205

Cys Gln Asp Ile Asn Glu Cys Glu His Arg Asn His Thr Cys Thr Ser
    210                 215                 220

Leu Gln Thr Cys Tyr Asn Leu Gln Gly Gly Phe Lys Cys Ile Asp Pro
225                 230                 235                 240

Ile Ser Cys Glu Glu Pro Tyr Leu Leu Ile Gly Glu Asn Arg Cys Met
                245                 250                 255

Cys Pro Ala Glu His Thr Ser Cys Arg Asp Gln Pro Phe Thr Ile Leu
            260                 265                 270

Tyr Arg Asp Met Asp Val Val Ser Gly Arg Ser Val Pro Ala Asp Ile
        275                 280                 285

Phe Gln Met Gln Ala Thr Thr Arg Tyr Pro Gly Ala Tyr Tyr Ile Phe
```

```
                290                 295                 300
Gln Ile Lys Ser Gly Asn Glu Gly Arg Glu Phe Tyr Met Arg Gln Thr
305                 310                 315                 320

Gly Pro Ile Ser Ala Thr Leu Val Met Thr Arg Pro Ile Lys Gly Pro
                325                 330                 335

Arg Asp Ile Gln Leu Asp Leu Glu Met Ile Thr Val Asn Thr Val Ile
            340                 345                 350

Asn Phe Arg Gly Ser Ser Val Ile Arg Leu Arg Ile Tyr Val Ser Gln
        355                 360                 365

Tyr Pro Phe
    370

<210> SEQ ID NO 13
<211> LENGTH: 162
<212> TYPE: DNA
<213> ORGANISM: Rattus norvegicus
<220> FEATURE:
<221> NAME/KEY: CDS
<222> LOCATION: (1)..(162)

<400> SEQUENCE: 13 cag caa cag tgc acc aac ggc ttt gac ctg gac cgc cag aca gga cag     48
Gln Gln Gln Cys Thr Asn Gly Phe Asp Leu Asp Arg Gln Thr Gly Gln
1               5                   10                  15 tgt tta gat att gat gaa tgt cgg acc atc cct gag gct tgc cgt ggg     96
Cys Leu Asp Ile Asp Glu Cys Arg Thr Ile Pro Glu Ala Cys Arg Gly
            20                  25                  30 gac atg atg tgt gtc aac cag aat ggc ggg tat ctg tgc atc cct cga    144
Asp Met Met Cys Val Asn Gln Asn Gly Gly Tyr Leu Cys Ile Pro Arg
        35                  40                  45 acc aac cca gtg tat cga                                            162
Thr Asn Pro Val Tyr Arg
    50

<210> SEQ ID NO 14
<211> LENGTH: 54
<212> TYPE: PRT
<213> ORGANISM: Rattus norvegicus

<400> SEQUENCE: 14

Gln Gln Gln Cys Thr Asn Gly Phe Asp Leu Asp Arg Gln Thr Gly Gln
1               5                   10                  15

Cys Leu Asp Ile Asp Glu Cys Arg Thr Ile Pro Glu Ala Cys Arg Gly
            20                  25                  30

Asp Met Met Cys Val Asn Gln Asn Gly Gly Tyr Leu Cys Ile Pro Arg
        35                  40                  45

Thr Asn Pro Val Tyr Arg
    50

<210> SEQ ID NO 15
<211> LENGTH: 1116
<212> TYPE: DNA
<213> ORGANISM: Rattus norvegicus
<220> FEATURE:
<221> NAME/KEY: CDS
<222> LOCATION: (1)..(1116)

<400> SEQUENCE: 15 ggg ccc tac tcc aat ccc tac tct aca tcc tac tca ggc cca tac cca     48
Gly Pro Tyr Ser Asn Pro Tyr Ser Thr Ser Tyr Ser Gly Pro Tyr Pro
1               5                   10                  15 gca gcc gca cca cca gtg cca gct tcc aac tac ccc acg att tcc agg     96
```

|  |  |
|---|---:|
| Ala Ala Ala Pro Val Pro Ala Ser Asn Tyr Pro Thr Ile Ser Arg<br>          20                     25                  30 |  |
| cct ctt gtc tgt cgc ttt ggg tat cag atg gat gaa ggc aac cag tgt<br>Pro Leu Val Cys Arg Phe Gly Tyr Gln Met Asp Glu Gly Asn Gln Cys<br>          35                     40                     45 | 144 |
| gtg gat gtg gac gag tgt gcg aca gat tca cac cag tgc aac cct acc<br>Val Asp Val Asp Glu Cys Ala Thr Asp Ser His Gln Cys Asn Pro Thr<br>50                       55                     60 | 192 |
| cag atc tgt atc aac acg gaa gga ggg tac acc tgc tcc tgc act gat<br>Gln Ile Cys Ile Asn Thr Glu Gly Gly Tyr Thr Cys Ser Cys Thr Asp<br>65                     70                   75                 80 | 240 |
| ggg tac tgg ctt ctg gaa ggg cag tgc cta gat att gat gaa tgt cgc<br>Gly Tyr Trp Leu Leu Glu Gly Gln Cys Leu Asp Ile Asp Glu Cys Arg<br>               85                     90                     95 | 288 |
| tat ggt tac tgc cag cag ctc tgt gcg aat gtt cct gga tcc tat tcc<br>Tyr Gly Tyr Cys Gln Gln Leu Cys Ala Asn Val Pro Gly Ser Tyr Ser<br>          100                    105                  110 | 336 |
| tgt acg tgt aac cct ggc ttc acc ctc aac gat gat gga agg tct tgc<br>Cys Thr Cys Asn Pro Gly Phe Thr Leu Asn Asp Asp Gly Arg Ser Cys<br>             115                  120                  125 | 384 |
| caa gat gtg aac gag tgt gaa act gag aac ccc tgt gtt cag acc tgc<br>Gln Asp Val Asn Glu Cys Glu Thr Glu Asn Pro Cys Val Gln Thr Cys<br>130                    135                  140 | 432 |
| gtc aac acc tat ggt tct ttc atc tgc cgc tgt gac cca gga tat gaa<br>Val Asn Thr Tyr Gly Ser Phe Ile Cys Arg Cys Asp Pro Gly Tyr Glu<br>145                    150                  155                  160 | 480 |
| ctg gag gaa gat ggc att cac tgc agt gat atg gat gag tgc agc ttc<br>Leu Glu Glu Asp Gly Ile His Cys Ser Asp Met Asp Glu Cys Ser Phe<br>               165                  170                  175 | 528 |
| tcc gag ttc ctc tgt caa cat gag tgt gtg aac cag ccg ggc tca tac<br>Ser Glu Phe Leu Cys Gln His Glu Cys Val Asn Gln Pro Gly Ser Tyr<br>             180                  185                  190 | 576 |
| ttc tgc tca tgc cct cca ggc tac gtc ttg ttg gaa gat aac cga agc<br>Phe Cys Ser Cys Pro Pro Gly Tyr Val Leu Leu Glu Asp Asn Arg Ser<br>          195                    200                  205 | 624 |
| tgc cag gat atc aat gaa tgt gag cac cgg aac cac aca tgc act ccc<br>Cys Gln Asp Ile Asn Glu Cys Glu His Arg Asn His Thr Cys Thr Pro<br>210                    215                  220 | 672 |
| ctg cag act tgc tac aat ctg caa ggg ggc ttc aaa tgt atc gac ccc<br>Leu Gln Thr Cys Tyr Asn Leu Gln Gly Gly Phe Lys Cys Ile Asp Pro<br>225                    230                  235                  240 | 720 |
| atc gtc tgc gag gag cct tat ctg ctg att ggg gat aac cgc tgt atg<br>Ile Val Cys Glu Glu Pro Tyr Leu Leu Ile Gly Asp Asn Arg Cys Met<br>               245                  250                  255 | 768 |
| tgc cct gct gag aat act ggc tgc agg gac cag cca ttc acc atc ttg<br>Cys Pro Ala Glu Asn Thr Gly Cys Arg Asp Gln Pro Phe Thr Ile Leu<br>          260                    265                  270 | 816 |
| ttt cgg gac atg gat gtg gta tca gga cgc tct gtt cct gct gac atc<br>Phe Arg Asp Met Asp Val Val Ser Gly Arg Ser Val Pro Ala Asp Ile<br>             275                  280                  285 | 864 |
| ttc cag atg caa gca acg acc cga tac cct ggc gcc tat tac att ttc<br>Phe Gln Met Gln Ala Thr Thr Arg Tyr Pro Gly Ala Tyr Tyr Ile Phe<br>290                    295                  300 | 912 |
| cag atc aaa tct ggg aac gag ggt cga gag ttc tac atg cgg caa aca<br>Gln Ile Lys Ser Gly Asn Glu Gly Arg Glu Phe Tyr Met Arg Gln Thr<br>305                    310                  315                  320 | 960 |
| ggg cct atc agt gcc acc ctg gtg atg aca cgc ccc atc aaa ggg cct<br>Gly Pro Ile Ser Ala Thr Leu Val Met Thr Arg Pro Ile Lys Gly Pro<br>             325                  330                  335 | 1008 |
| cgg gac atc cag ctg gac ttg gag atg atc acc gtc aac act gtc atc | 1056 |

```
Arg Asp Ile Gln Leu Asp Leu Glu Met Ile Thr Val Asn Thr Val Ile
        340                 345                 350 aac ttc aga ggc agc tcc gtg atc cga ctg cgg ata tac gtg tcc cag       1104
Asn Phe Arg Gly Ser Ser Val Ile Arg Leu Arg Ile Tyr Val Ser Gln
        355                 360                 365 tat ccg ttc tga                                                       1116
Tyr Pro Phe
    370

<210> SEQ ID NO 16
<211> LENGTH: 371
<212> TYPE: PRT
<213> ORGANISM: Rattus norvegicus

<400> SEQUENCE: 16

Gly Pro Tyr Ser Asn Pro Tyr Ser Thr Ser Tyr Ser Gly Pro Tyr Pro
1               5                   10                  15

Ala Ala Ala Pro Pro Val Pro Ala Ser Asn Tyr Pro Thr Ile Ser Arg
            20                  25                  30

Pro Leu Val Cys Arg Phe Gly Tyr Gln Met Asp Glu Gly Asn Gln Cys
        35                  40                  45

Val Asp Val Asp Glu Cys Ala Thr Asp Ser His Gln Cys Asn Pro Thr
50                  55                  60

Gln Ile Cys Ile Asn Thr Glu Gly Gly Tyr Thr Cys Ser Cys Thr Asp
65                  70                  75                  80

Gly Tyr Trp Leu Leu Glu Gly Gln Cys Leu Asp Ile Asp Glu Cys Arg
            85                  90                  95

Tyr Gly Tyr Cys Gln Gln Leu Cys Ala Asn Val Pro Gly Ser Tyr Ser
        100                 105                 110

Cys Thr Cys Asn Pro Gly Phe Thr Leu Asn Asp Asp Gly Arg Ser Cys
        115                 120                 125

Gln Asp Val Asn Glu Cys Glu Thr Glu Asn Pro Cys Val Gln Thr Cys
130                 135                 140

Val Asn Thr Tyr Gly Ser Phe Ile Cys Arg Cys Asp Pro Gly Tyr Glu
145                 150                 155                 160

Leu Glu Glu Asp Gly Ile His Cys Ser Asp Met Asp Glu Cys Ser Phe
            165                 170                 175

Ser Glu Phe Leu Cys Gln His Glu Cys Val Asn Gln Pro Gly Ser Tyr
        180                 185                 190

Phe Cys Ser Cys Pro Pro Gly Tyr Val Leu Leu Glu Asp Asn Arg Ser
        195                 200                 205

Cys Gln Asp Ile Asn Glu Cys Glu His Arg Asn His Thr Cys Thr Pro
210                 215                 220

Leu Gln Thr Cys Tyr Asn Leu Gln Gly Gly Phe Lys Cys Ile Asp Pro
225                 230                 235                 240

Ile Val Cys Glu Glu Pro Tyr Leu Leu Ile Gly Asp Asn Arg Cys Met
            245                 250                 255

Cys Pro Ala Glu Asn Thr Gly Cys Arg Asp Gln Pro Phe Thr Ile Leu
        260                 265                 270

Phe Arg Asp Met Asp Val Val Ser Gly Arg Ser Val Pro Ala Asp Ile
        275                 280                 285

Phe Gln Met Gln Ala Thr Thr Arg Tyr Pro Gly Ala Tyr Tyr Ile Phe
290                 295                 300

Gln Ile Lys Ser Gly Asn Glu Gly Arg Glu Phe Tyr Met Arg Gln Thr
305                 310                 315                 320

Gly Pro Ile Ser Ala Thr Leu Val Met Thr Arg Pro Ile Lys Gly Pro
```

325                 330                 335
Arg Asp Ile Gln Leu Asp Leu Glu Met Ile Thr Val Asn Thr Val Ile
            340                 345                 350

Asn Phe Arg Gly Ser Ser Val Ile Arg Leu Arg Ile Tyr Val Ser Gln
        355                 360                 365

Tyr Pro Phe
    370

<210> SEQ ID NO 17
<211> LENGTH: 173
<212> TYPE: DNA
<213> ORGANISM: Artificial
<220> FEATURE:
<223> OTHER INFORMATION: DNA encoding preprotrypsin signal peptide,
      FLAG tag, 6 x His tag and restriction sites

<400> SEQUENCE: 17
ggtaccgcta gcgaattcac catgtctgca cttctgatcc tagctcttgt tggagctgca      60
gttgctgact acaaagacga tgacgacaag actagtcatc atcaccatca ccattctaga    120
gaaggatccg atatccgcgg ccgcatcgat tgactagctg aggccgcaaa ccc           173

<210> SEQ ID NO 18
<211> LENGTH: 15
<212> TYPE: PRT
<213> ORGANISM: Artificial
<220> FEATURE:
<223> OTHER INFORMATION: preprotrypsin signal peptide

<400> SEQUENCE: 18

Met Ser Ala Leu Leu Ile Leu Ala Leu Val Gly Ala Ala Val Ala
1               5                   10                  15

<210> SEQ ID NO 19
<211> LENGTH: 8
<212> TYPE: PRT
<213> ORGANISM: Artificial
<220> FEATURE:
<223> OTHER INFORMATION: FLAG tag

<400> SEQUENCE: 19

Asp Tyr Lys Asp Asp Asp Asp Lys
1               5

<210> SEQ ID NO 20
<211> LENGTH: 6
<212> TYPE: PRT
<213> ORGANISM: Artificial
<220> FEATURE:
<223> OTHER INFORMATION: 6 x His tag

<400> SEQUENCE: 20

His His His His His His
1               5

<210> SEQ ID NO 21
<211> LENGTH: 105
<212> TYPE: DNA
<213> ORGANISM: Artificial
<220> FEATURE:
<223> OTHER INFORMATION: DNA encoding preprotrypsin signal peptide,
      Myc tag and restriction sites

<400> SEQUENCE: 21
gaattcacca tgtctgcact tctgatccta gctcttgttg gagctgcagt tgctgactac      60

```
gaagaggacg aacaaaaact catctcagaa gaggatctga ctagt            105
```

<210> SEQ ID NO 22
<211> LENGTH: 10
<212> TYPE: PRT
<213> ORGANISM: Artificial
<220> FEATURE:
<223> OTHER INFORMATION: Myc tag
<400> SEQUENCE: 22

```
Glu Gln Lys Leu Ile Ser Glu Glu Asp Leu
1               5                   10
```

<210> SEQ ID NO 23
<211> LENGTH: 143
<212> TYPE: DNA
<213> ORGANISM: Artificial
<220> FEATURE:
<223> OTHER INFORMATION: DNA encoding FLAG tag, 6 x His tag and
      restriction sites <400> SEQUENCE: 23

```
tggtaccgag ctcggatcca ctagtccagt gtggtggaat tctgcagata tccagcacag    60
tggcggccgt ctagagacta caaagacgat gacgacaaga gagggtctca tcatcaccat   120
caccattgag cggccgcaaa ccc                                           143
```

<210> SEQ ID NO 24
<211> LENGTH: 28
<212> TYPE: DNA
<213> ORGANISM: Artificial
<220> FEATURE:
<223> OTHER INFORMATION: PCR primer for amplifying human DANCE
<400> SEQUENCE: 24

```
tctagagcac agtgcacgaa tggctttg                                       28
```

<210> SEQ ID NO 25
<211> LENGTH: 38
<212> TYPE: DNA
<213> ORGANISM: Artificial
<220> FEATURE:
<223> OTHER INFORMATION: PCR primer for amplifying human DANCE
<400> SEQUENCE: 25

```
gcggccggtc agaatgggta ctgcgacaca tatatccg                            38
```

<210> SEQ ID NO 26
<211> LENGTH: 33
<212> TYPE: DNA
<213> ORGANISM: Artificial
<220> FEATURE:
<223> OTHER INFORMATION: PCR primer for amplifying human LTBP2

<400> SEQUENCE: 26

```
tctagacaaa gggacccccgt agggagatac gag                                33
```

<210> SEQ ID NO 27
<211> LENGTH: 34
<212> TYPE: DNA
<213> ORGANISM: Artificial
<220> FEATURE:
<223> OTHER INFORMATION: PCR primer for amplifying human LTBP2

<400> SEQUENCE: 27

```
gcggccgcct ggtactcctt ggcagtgcag tggg                                34
```

```
<210> SEQ ID NO 28
<211> LENGTH: 31
<212> TYPE: DNA
<213> ORGANISM: Artificial
<220> FEATURE:
<223> OTHER INFORMATION: PCR primer for amplifying human DANCE

<400> SEQUENCE: 28
gaattcttct tctcgccttc gcatctcctc c                              31

<210> SEQ ID NO 29
<211> LENGTH: 33
<212> TYPE: DNA
<213> ORGANISM: Artificial
<220> FEATURE:
<223> OTHER INFORMATION: PCR primer for amplifying human DANCE

<400> SEQUENCE: 29
tctagagaat gggtactgcg acacatatat ccg                            33
```